(12) United States Patent
Maienfisch et al.

(10) Patent No.: US 6,353,001 B1
(45) Date of Patent: Mar. 5, 2002

(54) 2-NITROMETHYLIDENE/2-CYANIMINO/2-NITRO-IMINO-PYRROLIDINES AND PIPERIDINES, INTERMEDIATES, AND THEIR USE AS PESTICIDES

(75) Inventors: Peter Maienfisch, Rodersdorf (CH); Jozef Gonda, Kosice (SK); Olivier Jacob, Rantzwiller (FR); Laurenz Gsell, Basel (CH)

(73) Assignee: Syngenta Investment Corporation, Wilimington, DE (US)

( * ) Notice: Subject to any disclaimer, the term of this patent is extended or adjusted under 35 U.S.C. 154(b) by 0 days.

(21) Appl. No.: 09/501,464

(22) Filed: Feb. 9, 2000

Related U.S. Application Data

(62) Division of application No. 08/532,553, filed as application No. PCT/EP94/00963 on Mar. 26, 1994, now Pat. No. 6,048,824.

(30) Foreign Application Priority Data

Apr. 8, 1993 (CH) .................................. 1074/93

(51) Int. Cl.$^7$ ..................... A61K 31/44; C07D 211/00
(52) U.S. Cl. .................. 514/315; 514/345; 514/183; 546/243; 546/246
(58) Field of Search .............................. 514/315, 345, 514/183; 546/243, 246

(56) References Cited

U.S. PATENT DOCUMENTS

| | | | |
|---|---|---|---|
| 3,714,183 A | 1/1973 | Vail ........................... | 548/519 |
| 3,823,152 A | 7/1974 | Morimoto et al. .......... | 546/193 |
| 3,853,888 A | 12/1974 | Roman ....................... | 546/246 |
| 3,950,530 A | 4/1976 | Horne, Jr. .................. | 514/328 |
| 5,302,605 A | 4/1976 | Horne, Jr. .................. | 514/341 |
| 4,742,060 A | 5/1988 | Shiokawa et al. .......... | 514/252 |
| 4,849,432 A | 7/1989 | Shiokawa et al. .......... | 514/341 |
| 4,933,463 A | 6/1990 | Dandreaux et al. ......... | 548/238 |
| 5,270,339 A | 12/1993 | Yamanoto et al. .......... | 514/408 |
| 5,298,507 A | 3/1994 | Shiokawa et al. .......... | 514/256 |

FOREIGN PATENT DOCUMENTS

| | | |
|---|---|---|
| DE | 2138331 | 2/1972 |
| EP | 0192060 | 8/1986 |
| EP | 0235725 | 9/1987 |
| EP | 0483052 | 4/1992 |
| GB | 1024400 | 3/1966 |

OTHER PUBLICATIONS

Chem. Abst. 84:30358z, Cuuigny et al., p. 403 (1976).
Collection Czechoslov, Chem. Commun., vol. 38, J. Kondelikova et al., pp. 523–531 (1973).
Adv. Pest. Sci., 4th Intern. Congr. Pest. Chem., Part 2, pp. 206–207, Geissbuhler (1978).
Tetra. Lett., vol. 23, No. 50, pp. 5319–5322 (1982).
Wesbster's II: New Riverside University Dictionary, 1994, Houghton Mifflin Co., p. 878.
J. Pesticides Sci. 18, pp. 91–98 (1993) Tomizawa et al.

Primary Examiner—Mukund J. Shah
Assistant Examiner—Sudhaker B. Patel
(74) Attorney, Agent, or Firm—William A. Teoli, Jr.

(57) ABSTRACT

Compounds of formula:

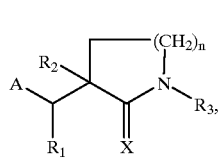

(I)

wherein

A is an unsubstituted or substituted aromatic or non-aromatic, monocyclic or bicyclic heterocyclic radical wherein a ring nitrogen atom may have been replaced by a group

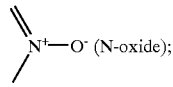

$R_1$ is hydrogen or $C_1$–$C_3$alkyl;

$R_2$ is hydrogen or $C_1$–$C_3$alkyl;

$R_3$ is hydrogen, an unsubstituted or substituted $C_1$–$C_6$alkyl, $C_3$–$C_6$cycloalkyl, $C_2$–$C_6$alkenyl or $C_2$–$C_6$alkynyl group, or C(=O)—$R_5$, $R_5$ is $C_1$–$C_4$alkyl, $C_1$–$C_4$alkoxy, an unsubstituted or substituted phenyl, phenoxy or benzyloxy group, or N($R_6$)$_2$, each $R_6$, independently of the other, is hydrogen, $C_1$–$C_4$alkyl or unsubstituted or substituted phenyl, X is CH—$NO_2$, N—CN or N—$NO_2$ and n is from 1 to 3, in free form or in salt form, and, where appropriate, tautomers of those compounds and the salts thereof, can be used as agrochemical active ingredients and can be prepared in a manner known per se.

30 Claims, No Drawings

2-NITROMETHYLIDENE/2-CYANIMINO/2-NITRO-IMINO-PYRROLIDINES AND PIPERIDINES, INTERMEDIATES, AND THEIR USE AS PESTICIDES

This application is a division of Ser. No. 08/532,553, filed Nov. 22, 1995 (now U.S. Pat. No. 6,048,824), which is a 371 of international application PCT/EP94/00963, filed Mar. 26, 1994.

The invention relates to compounds of formula:

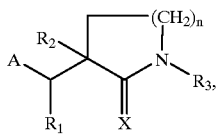

(I)

wherein

A is an unsubstituted or substituted aromatic or non-aromatic, monocyclic or bicyclic heterocyclic radical wherein a ring nitrogen atom may have been replaced by a group

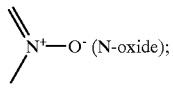

$R_1$ is hydrogen or $C_1$–$C_3$alkyl;

$R_2$ is hydrogen or $C_1$–$C_3$alkyl;

$R_3$ is hydrogen, an unsubstituted or substituted $C_1$–$C_6$alkyl, $C_3$–$C_6$cycloalkyl, $C_2$–$C_6$alkenyl or $C_2$–$C_6$alkynyl group, or C(=O)—$R_5$, $R_5$ is $C_1$–$C_4$alkyl, $C_1$–$C_4$alkoxy, an unsubstituted or substituted phenyl, phenoxy or benzyloxy group, or N($R_6$)$_2$, each $R_6$, independently of the other, is hydrogen, $C_1$–$C_4$alkyl or unsubstituted or substituted phenyl, X is CH—$NO_2$, N—CN or N—$NO_2$ and n is from 1 to 3, in free form or in salt form, where appropriate to tautomers of those compounds and to the salts thereof, to processes for the preparation of those compounds and tautomers and to the use thereof, to pesticidal compositions comprising an active ingredient selected from those compounds and tautomers, to a process for the preparation of those compositions and to the use thereof, to plant propagation material treated with those compositions, to a method of controlling pests, to intermediates and, where appropriate, the tautomers thereof, in each case in free form or in salt form, to processes for the preparation of those active ingredients and to processes for the preparation of those intermediates and the tautomers thereof.

The invention relates especially to compounds c: formula I wherein

A is an unsubstituted or mono- to tetra-substituted aromatic or non-aromatic, mono-cyclic or bicyclic heterocyclic radical wherein a ring nitrogen atom may have been replaced by a group

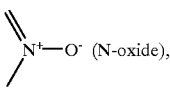

and wherein one or two of the substituents of A may be selected from the group consisting of $C_1$–$C_3$alkyl, halo-$C_1$–$C_3$alkyl, cyclopropyl, halocyclopropyl, $C_2$–$C_3$alkenyl, $C_2$–$C_3$alkynyl, halo-$C_2$–$C_3$alkenyl, halo-$C_2$–$C_3$alkynyl, hydroxy, mercapto, halo-$C_1$–$C_3$alkoxy, $C_1$–$C_3$allylthio, halo-$C_1$–$C_3$alkylthio, allyloxy, propargyloxy, allylthio, propargylthio, haloallyloxy, haloallylthio, cyano and nitro, and from one to four of the substituents of A may be selected from the group consisting of $C_1$–$C_3$alkyl, $C_1$–$C_3$alkoxy and halogen;

$R_1$ is hydrogen or $C_1$–$C_3$alkyl;

$R_2$ is hydrogen or $C_1$–$C_3$alkyl;

$R_3$ is hydrogen, $C_1$–$C_6$alkyl, halo-$C_1$–$C_6$alkyl, $C_1$–$C_6$alkoxy-$C_1$–$C_6$alkyl, $C_1$–$C_6$alkylthio-$C_1$–$C_6$alkyl, phenoxy-$C_1$–$C_6$alkyl, phenylthio-$C_1$–$C_6$alkyl, $C_3$–$C_6$cycloalkyl-$C_1$–$C_6$alkyl, benzyloxy-$C_1$–$C_6$alkyl, di($C_1$–$C_4$alkyl)amino-$C_1$–$C_6$alkyl, cyano-$C_1$–$C_6$alkyl, $C_1$–$C_4$alkylcarbonyl-$C_1$–$C_6$alkyl, $C_1$–$C_4$alkoxycarbonyl-$C_1$–$C_6$alkyl, $C_3$–$C_6$cycloalkyl, halo-$C_3$–$C_6$cycloalkyl, $C_2$–$C_6$alkenyl, halo-$C_2$–$C_6$alkenyl, $C_2$–$C_6$alkynyl, halo-$C_2$–$C_6$alkynyl or C(=O)—$R_5$, $R_5$ is $C_1$–$C_4$alkyl, $C_1$–$C_4$alkoxy, phenyl, phenoxy or benzyloxy, or phenyl, phenoxy or benzyloxy substituted by from one to three substituents selected from the group consisting of halogen, $C_1$–$C_4$alkyl, halo-$C_1$–$C_4$alkyl, $C_1$–$C_4$alkoxy, nitro and cyano, or is N($R_6$)$_2$, each $R_6$, independently of the other, is hydrogen, $C_1$–$C_4$alkyl or phenyl, or phenyl substituted by from one to three substituents selected from the group consisting of halogen, $C_1$–$C_4$alkyl, halo-$C_1$–$C_4$alkyl, $C_1$–$C_4$alkoxy, nitro and cyano, X is CH—$NO_2$, N—CN or N—$NO_2$ and n is from 1 to 3, and the tautomers thereof, in each case in free form or in salt form.

Certain 3-substituted 2-nitromethylidene-piperidines and 2-nitromethylidene-pyrrolidines are proposed in the literature as arthropodicidal active ingredients in pesticides. The biological properties of those known compounds are not, however, fully satisfactory in the area of pest control and there is therefore a need to provide further compounds having pest-control properties, especially for controlling insects. That problem is solved according to the invention by the provision of the present compounds of formula I.

Some of the compounds of formula I can be in the form of tautomers. That relates, for example, to the heterocyclic radicals A that are substituted by a hydroxy group or by a mercapto group wherein, depending on the structure, the hydroxy or the oxo form, or the mercapto or the thioxo form, respectively, may be present, or the two tautomeric forms may be present alongside one another.

Compounds of formula I having at least one basic centre are capable of forming acid addition salts. Those salts are formed, for example, with strong inorganic acids, such as mineral acids, for example perchloric acid, sulfuric acid, nitric acid, nitrous acid, a phosphoric acid or a hydrohalic acid, with strong organic carboxylic acids, such as unsubstituted or substituted, for example halo-substituted, $C_1$–$C_4$alkanecarboxylic acids, for example acetic acid, or saturated or unsaturated dicarboxylic acids, for example oxalic, malonic, succinic, maleic, fumaric or phthalic acid, or hydroxycarboxylic acids, for example ascorbic, lactic, malic, tartaric or citric acid, or benzoic acid, or with organic sulfonic acids, such as unsubstituted or substituted, for example halo-substituted, $C_1$–$C_4$alkanesulfonic or arylsulfonic acids, for example methanesulfonic or p-toluenesulfonic acid. Furthermore, compounds of formula I having at least one acidic group are capable of forming salts with bases. Suitable salts with bases are, for example, metal salts, such as alkali metal or alkaline earth metal salts, for example sodium, potassium or magnesium salts, or salts with ammonia or an organic amine, such as morpholine, piperidine, pyrrolidine, a mono-, di- or tri-lower alkylamine, for example ethylamine, diethylamine, triethylamine or dimethylpropylamine, or a mono-, di- or tri-hydroxy-lower alkylamine, for example mono-, di- or tri-ethanolamine. Where appropriate, corresponding internal salts may be formed. Preference is given within the scope of the invention to agrochemically acceptable salts, but salts that have disadvantages for agrochemical purposes are also included; they are used, for example, in the isolation or purification of free compounds of formula I or the agrochemically acceptable salts thereof. Hereinbefore and hereinafter, the expression "compound(s) of formula I" thus always also includes the salts of those compounds, their tautomers and the salts of the tautomers.

Suitable as heteroatoms in the basic ring structure of the heterocyclic radical A are any elements of the Periodic Table that are capable of forming at least two covalent bonds, but preference is given to oxygen, nitrogen and sulfur, especially nitrogen and sulfur, more especially nitrogen.

Halogen—per se and as a structural element of other groups and compounds, such as haloalkyl, haloalkylthio, haloalkoxy, halocyclopropyl, haloalkenyl, haloalkynyl, haloallyloxy and haloallylthio—is fluorine, chlorine, bromine or iodine, especially fluorine, chlorine or bromine, more especially fluorine or chlorine and most especially chlorine.

Unless otherwise defined, carbon-containing groups and compounds each contain from 1 up to and including 6, preferably from 1 up to and including 3, more especially 1 or 2, carbon atoms.

Cycloalkyl is cyclopropyl, cyclobutyl, cyclopentyl or cyclohexyl, preferably cyclopropyl.

Alkyl—as a group per se and as a structural element of other groups and compounds, such as haloalkyl, alkoxy, haloalkoxy, alkylthio and haloalkylthio—in each case taking due account of the number of carbon atoms in the group or compound in question—is either straight-chained, i.e. methyl, ethyl, propyl, butyl, pentyl or hexyl, or branched, e.g. isopropyl, isobutyl, sec-butyl, tert-butyl, isopentyl, neopentyl or isohexyl.

Alkenyl, haloalkenyl, alkynyl and haloalkynyl are straight-chained or branched and each contain two or preferably one unsaturated carbon-carbon bond(s). The double or triple bonds of those substituents are separated from the remainder of the compound of formula I preferably by at least one saturated carbon atom. The following may be mentioned by way of example: allyl, methallyl, but-2-enyl, but-3-enyl, propargyl, but-2-ynyl and but-3-ynyl.

Halo-substituted carbon-containing groups and compounds, such as haloalkyl, haloalkylthio, haloalkoxy, halocycloalkyl, haloalkenyl, haloalkynyl, haloallyloxy and haloallylthio, may be partially halogenated or perhalogenated, it being possible in the case of polyhalogenation for the halogen substituents to be identical or different. Examples of haloalkyl—as a group per se and as a structural element of other groups and compounds, such as haloalkylthio and haloalkoxy—are methyl mono- to tri-substituted by fluorine, chlorine and/or by bromine, such as $CHF_2$ or $CF_3$; ethyl mono- to penta-substituted by fluorine, chlorine and/or by bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; and propyl or isopropyl mono- to hepta-substituted by fluorine, chlorine and/or by bromine, such as $CH_2CHBrCH_2Br$, $CF_2CHFCF_3$, $CH_2CF_2CF_3$, $CF_2CF_2CF_3$ or $CH(CF_3)_2$. Examples of haloalkenyl are 2,2-diflhoroethen-1-yl, 2,2-dichloroethen-1-yl, 2-chloroprop-2-en-1-yl, 2,3-dichloroprop-2-en-1-yl and 2,3-dibromoprop-2-en-1-yl. Examples of haloalkynyl are 2-chloroprop-2-yn-1-yl, 2,3-dichloroprop-2-yn-1-yl and 2,3-dibromoprop-2-yn-1-yl. Examples of halocyclopropyl are 2-chlorocyclopropyl, 2,2-difluorocyclopropyl and 2-chloro-2-fluoro-cyclopropyl. Examples of haloallyloxy are 2-chloroprop-2-en-1-yloxy, 2,3-dichloroprop-2-en-1-yloxy and 2,3-dibromoprop-2-en-1-yloxy. Examples of haloallylthio are 2-chloroprop-2-en-1-ylthio, 2,3-dichloroprop-2-en-1-ylthio and 2,3-dibromoprop-2-en-1-ylthio.

$C_1$–$C_6$Alkoxy-$C_1$–$C_6$alkyl, phenoxy-$C_1$–$C_6$alkyl, phenylthio-$C_1$–$C_6$alkyl, $C_3$–$C_6$cycloalkyl-$C_1$–$C_6$alkyl, benzyloxy-$C_1$–$C_6$alkyl, di($C_1$–$C_4$alkyl)amino-$C_1$–$C_6$alkyl, cyano-$C_1$–$C_6$alkyl, $C_1$–$C_4$alkylcarbonyl-$C_1$–$C_6$alkyl, $C_1$–$C_4$alkoxycarbonyl-$C_1$–$C_6$alkyl and $C_1$–$C_6$alkylthio-$C_1$–$C_6$alkyl are alkyl groups mono-substituted by alkoxy, phenoxy, phenylthio, $C_3$–$C_6$cycloalkyl, benzyloxy, di($C_1$–$C_4$alkyl)amino, cyano, $C_1$–$C_4$alkylcarbonyl, $C_1$–$C_4$alkoxycarbonyl or by alkylthio, it being possible for the two carbon chains each independently of the other to be straight or branched. Examples are methoxymethyl, 2-methoxyethyl, ethoxymethyl, 2-isopropoxyethyl, 2-propoxypropyl, 4methoxybut-2-yl, 2-methylthioethyl, ethylthiomethyl, phenoxymethyl, 2-cyanoethyl, dimethylaminomethyl and cyclopropylmethyl.

Preferred embodiments within the scope of the invention are:

(1) A compound of formula I wherein
    A is an unsubstituted or mono- to tetra-substituted aromatic or non-aromatic, monocyclic or bicyclic heterocyclic radical, wherein one or two of the substituents of A may be selected from the group consisting of halo-$C_1$–$C_3$alkyl, cyclopropyl, halocyclopropyl, $C_2$–$C_3$alkenyl, $C_2$–$C_3$alkynyl, halo-$C_2$–$C_3$alkenyl, halo-$C_2$–$C_3$alkynyl, halo-$C_1$–$C_3$alkoxy, $C_1$–$C_3$alkylthio, halo-$C_1$–$C_3$alkylthio, allyloxy, propargyloxy, allylthio, propargylthio, haloallyloxy, haloallylthio, cyano and nitro, and from one to four of the substituents of A may be selected from the group consisting of $C_1$–$C_3$alkyl, $C_1$–$C_3$alkoxy and halogen;
    $R_1$ is hydrogen or $C_1$–$C_3$alkyl;
    $R_2$ is hydrogen or $C_1$–$C_3$alkyl;
    $R_3$ is hydrogen, $C_1$–$C_6$alkyl, $C_3$–$C_6$cycloalkyl, $C_2$–$C_6$alkenyl or $C_2$–$C_6$alkynyl;
    X is CH—$NO_2$ or N—CN, and
    n is from 1 to 3;

(2) a compound of formula I in free form;

(3) a compound of formula I wherein the basic ring structure of A consists of a ring having 5 or 6 ring members to which a further ring having 5 or 6 ring members may have been fused, especially of a ring having 5 or 6, preferably 6, ring members;

(4) a compound of formula I wherein the basic ring structure of A is unsaturated and contains especially from 1 to 4, preferably from 2 to 4, double bonds, preferably conjugated double bonds, and is especially of aromatic character;

(5) a compound of formula I wherein the basic ring structure of A contains 1, 2 or 3 hetero atoms selected from the group consisting of oxygen, sulfur and nitrogen, not more than one of the hetero atoms in the basic ring structure being an oxygen atom and not more than one of the hetero atoms in the basic ring structure being a sulfur atom, especially 1 or 2 hetero atoms selected from the group consisting of oxygen, sulfur and nitrogen, not more than one of the hetero atoms in the basic ring structure being an oxygen atom or a sulfur atom, preferably a nitrogen atom;

(6) a compound of formula I wherein A is selected from the group of heterocycles consisting of:

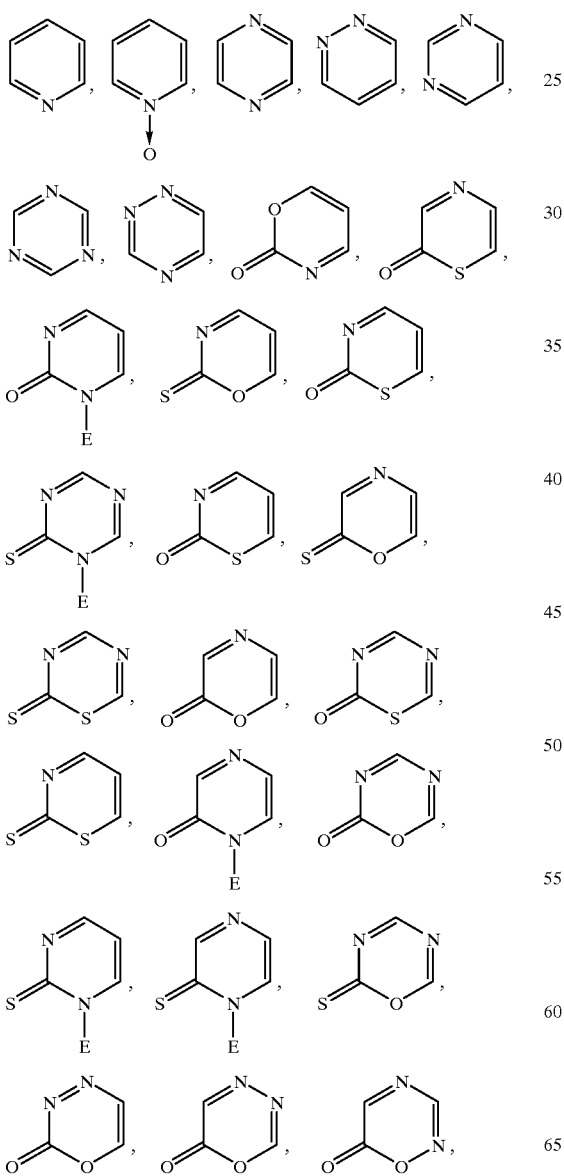

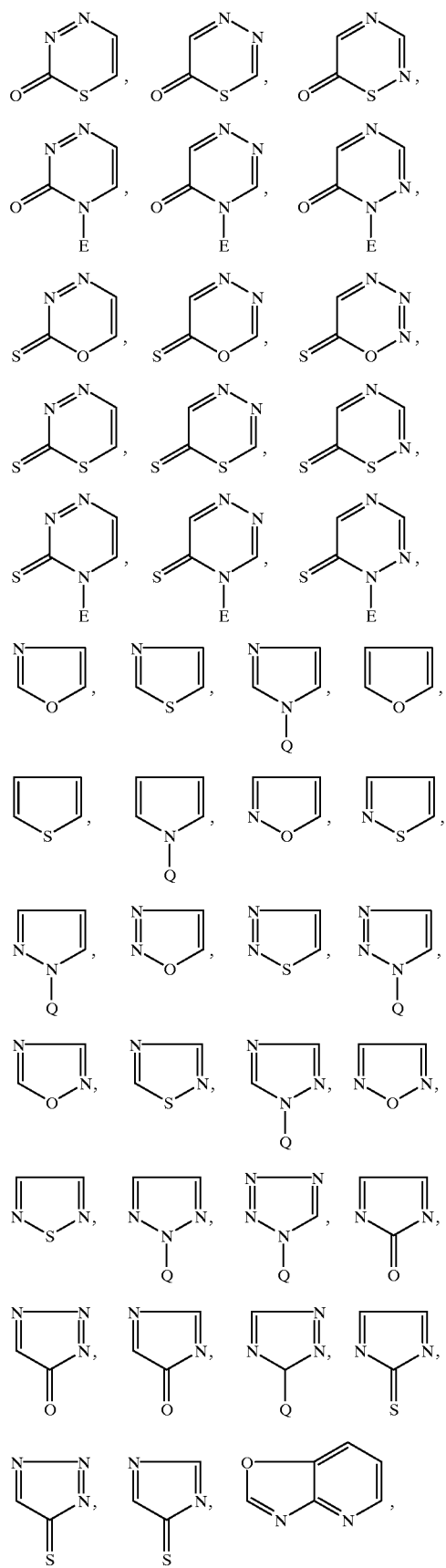

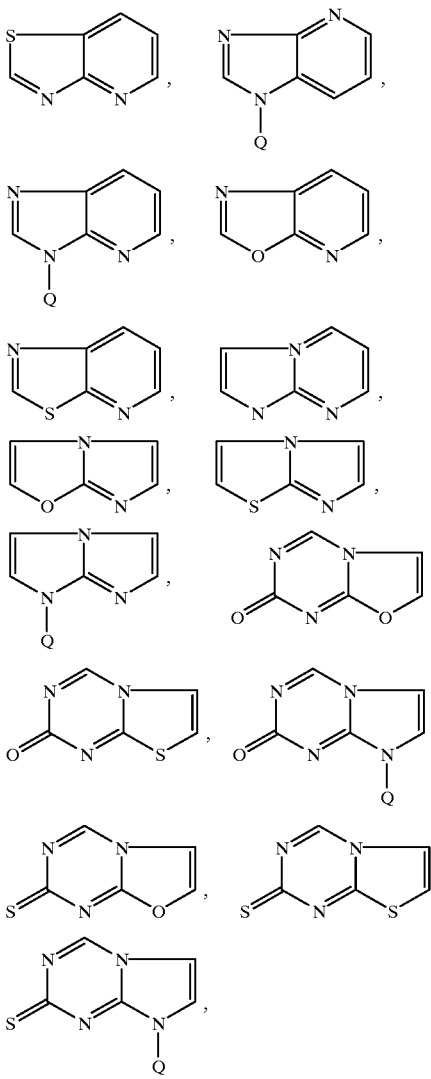

wherein E is $C_1$–$C_3$alkyl and Q is hydrogen, $C_1$–$C_3$alkyl or cyclopropyl, or, where appropriate, a tautomer thereof;

(7) a compound of formula I wherein A is bonded via a carbon atom of its basic ring structure to the remainder of the compound of formula I;

(8) a compound of formula I wherein A is unsubstituted or mono- or di-substituted by substituents selected from the group consisting of halogen, —OH, —SH, $C_1$–$C_3$alkyl, halo-$C_1$–$C_3$alkyl, $C_1$–$C_3$alkoxy and halo-$C_1$–$C_3$alkoxy, and a ring nitrogen atom of A may have been replaced by preferably unsubstituted or mono- or di-substituted by substituents selected from the group consisting of halogen and $C_1$–$C_3$alkyl, and a ring nitrogen atom of A may have been replaced by especially mono-substituted by halogen, more especially mono-substituted by chlorine;

(9) a compound of formula I wherein A is pyridyl, 1-oxidopyridinio or thiazolyl, each of which may be unsubstituted or substituted, preferably pyrid-3-yl, 1-oxido-3-pyridinio or thiazol-5-yl, each of which may be unsubstituted or substituted, especially pyrid-3-yl, 2-halopyrid-5-yl, 2,3-dihalopyrid-5-yl, 2-($C_1$–$C_3$alkyl)pyrid-5-yl, 1-oxido-3-pyridinio, 2-halo-1-oxido-5-pyridinio, 2,3-dihalo-1-oxido-5-pyridinio or 2-halothiazol-5-yl, more especially pyrid-3-yl, 2-halopyrid-5-yl, 2-halo-1-oxido-5-pyridinio or 2-halothiazol-5-yl, preferably 2-chloropyrid-5-yl, 2-methylpyrid-5-yl, 1-oxido-3-pyridinio, 2-chloro-1-oxido-5-pyridinio, 2,3-dichloro-1-oxido-5-pyridinio or 2-chlorothiazol-5-yl, especially pyrid-3-yl, 2-chloropyrid-5-yl, 2-chloro-1-oxido-5-pyridinio or 2-chlorothiazol-5-yl, more especially 2-chlorothiazol-5-yl or 2-chloropyrid-5-yl, most especially 2-chloropyrid-5-yl;

(10) a compound of formula I wherein $R_1$ is hydrogen or methyl, especially hydrogen;

(11) a compound of formula I wherein $R_2$ is hydrogen or methyl, especially hydrogen;

(12) a compound of formula I wherein $R_3$ is hydrogen, $C_1$–$C_6$alkyl, halo-$C_1$–$C_6$alkyl, $C_1$–$C_6$alkoxy-$C_1$–$C_6$alkyl, phenoxy-$C_1$–$C_6$alkyl, benzyloxy-$C_1$–$C_6$alkyl, di($C_1$–$C_4$alkyl)amino-$C_1$–$C_6$alkyl, cyano-$C_1$–$C_6$alkyl, $C_1$–$C_4$alkylcarbonyl-$C_1$–$C_6$alkyl, $C_1$–$C_4$alkoxycarbonyl-$C_1$–$C_6$alkyl, $C_3$–$C_6$cycloalkyl, $C_2$–$C_6$alkenyl, $C_2$–$C_6$alkynyl, $C(=O)$-$C_1$–$C_4$alkyl, $C(=O)$—O—$C_1$–$C_4$alkyl or $N(R_6)_2$ and each $R_6$, independently of the other, is hydrogen, $C_1$–$C_4$alkyl or phenyl;

$R_3$ being especially hydrogen, $C_1$–$C_6$alkyl, $C_3$–$C_6$cycloalkyl, $C_3$–$C_4$alkenyl or $C_3$–$C_4$alkynyl, preferably hydrogen, $C_1$–$C_4$alkyl or $C_3$–$C_6$cycloalkyl, especially hydrogen or $C_1$–$C_4$alkyl, preferably methyl;

(13) a compound of formula I wherein X is CH—$NO_2$;

(14) a compound of formula I wherein X is N—CN;

(15) a compound of formula I wherein n is 1 or 2, especially 1;

(16) a compound of formula I wherein

A is a pyridyl, 1-oxidopyridinio or thiazolyl group bonded via a carbon atom of its basic ring structure to the remainder of the compound of formula I and unsubstituted or mono- or di-substituted by substituents selected from the group consisting of halogen and $C_1$–$C_3$alkyl, $R_1$ and $R_2$ are each independently of the other hydrogen or methyl, $R_3$ is hydrogen, $C_1$–$C_6$alkyl, $C_3$–$C_6$cycloalkyl, $C_3$–$C_4$alkenyl or $C_3$–$C_4$alkynyl, n is 1 or 2 and X is CH—NO$_2$ or N—CN;

(17) a compound of formula I wherein

A is pyrid-3-yl, 2-chloropyrid-5-yl, 1-oxido-3-pyridinio, 2-chloro-1-oxido-5-pyridinio, 2,3-dichloro-1-oxido-5-pyridinio or 2-chlorothiazol-5-yl, R$_1$ and R$_2$ are each independently of the other hydrogen or methyl, R$_3$ is hydrogen or C$_1$–C$_4$alkyl, n is 1 or 2 and X is CH—NO$_2$ or N—CN;

(18) a compound of formula I wherein

A is 2-chlorothiazol-5-yl or 2chloropyrid-5-yl,

R$_1$ and R$_2$ are hydrogen,

R$_3$ is hydrogen or C$_1$–C$_4$alkyl, n is 1 or 2 and

X is CH—NO$_2$;

(19) a compound of formula I wherein

A is 2-chlorothiazol-5-yl or 2-chloropyrid-5-yl,

R$_1$ and R$_2$ are hydrogen,

R$_3$ is hydrogen or C$_1$–C$_4$alkyl, n is 1 or 2 and

X is N—CN;

(20) a compound of formula I wherein

A is 2-chlorothiazol-5-yl or 2-chloropyrid-5-yl,

R$_1$ and R$_2$ are hydrogen,

R$_3$ is hydrogen or C$_1$–C$_4$alkyl, n is 1 or 2 and

X is N—NO$_2$.

Within the scope of the invention, special preference is given to the compounds of formula I mentioned in Examples P15, P18 and P19.

Within the scope of the invention, preference is given specifically to:

(a) 3-(2-chloropyrid-5-yl-methyl)-1-methyl-2-nitromethylidene-pyrrolidine, (b) 3-(2-chloropyrid-5-yl-methyl)-2-nitromethylidene-pyrrolidine, (c) 3-(2-chlorothiazol-5-yl-methyl)-1-methyl-2-nitromethylidene-pyrrolidine, (d) 3-(2-chlorothiazol-5-yl-methyl)-2-nitromethylidene-pyrrolidine, (e) 3-(2-chloropyrid-5-yl-methyl)-1-methyl-2-nitromethylidene-piperidine, (f) 3-(2-chloropyrid-5-yl-methyl)-2-nitromethylidene-piperidine, (g) 3-(2-chlorothiazol-5-yl-methyl)-1-methyl-2-nitromethylidene-piperidine, (h) 3-(2-chlorothiazol-5-yl-methyl)-2-nitromethylhdene-piperidine, (i) 3-(2-chloropyrid-5-yl-methyl)-1-methyl-2-cyanimino-pyrrolidine, (k) 3-(2-chloropyrid-5-yl-methyl)-2yanimino-pyrrolidine, (l) 3-(2-chlorothiazol-5-yl-methyl)-1-methyl-2-cyanimino-pyrrolidine, (m) 3-(2-chlorothiazol-5-yl-methyl)-2-cyanimino-pyrrolidine, (n) 3-(2-chloropyrid-5-yl-methyl)-1-methyl-2-cyanimino-piperidine, (o) 3-(2-chloropyrid-5-yl-methyl)-2-cyanimino-piperidine, (p) 3-(2-chlorothiazol-5yl-methyl) l-methyl-2-cyanimino-piperidine and (q) 3-(2-chlorothiazol-5-yl-methyl)2-cyanimino-piperidine.

The invention relates further to a process for the preparation of a compound of formula I which comprises either reacting a) a compound of formula;

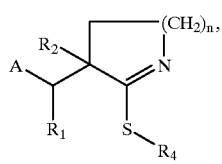

(IIa)

wherein A, R$_1$, R$_2$ and n are as defined above for formula I and R$_4$ is C$_1$–C$_6$alkyl, or a tautomer and/or a salt thereof, or b) for the preparation of a compound of formula I wherein R$_3$ is other than hydrogen, a salt of formula:

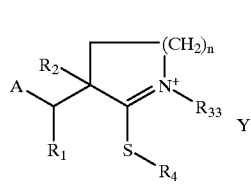

(IIb)

wherein A, R$_1$, R$_2$ and n are as defined above for formula I, R$_{33}$ has the definitions given for R$_3$ in formula I with the exception of hydrogen, R$_4$ is C$_1$–C$_6$alkyl and Y$^-$ is a counter ion, preferably a halide or a sulfate, or, where appropriate, a tautomer thereof, or c) a compound of formula:

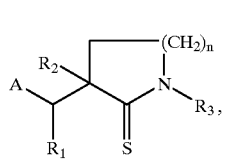

(III)

wherein A, R$_1$, R$_2$, R$_3$ and n are as defined above for formula I, or a tautomer and/or a salt thereof, with nitromethane, cyanamide, a salt of nitromethane or of cyanamide, where appropriate in the presence of a base, or with ammonia and a nitration reagent, where appropriate in the presence of an acid, or d) for the preparation of a compound of formula I wherein R$_3$ is other than hydrogen, reacting a compound of formula:

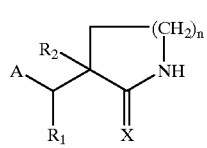

(Ia)

(obtainable, for example, in accordance with process a) or c)), wherein A, R$_1$, R$_2$, X and n are as defined above for formula I, or a salt thereof, with a compound of formula:

Y—R₃₃ (IV), wherein $R_{33}$ has the definitions given for $R_3$ in formula I with the exception of hydrogen, and Y is a leaving group, and/or, if desired, converting a compound of formula I obtainable in accordance with the process or by another method, or a tautomer thereof, in each case in free form or in salt form, into a different compound of formula I or a tautomer thereof, separating a mixture of isomers obtainable in accordance with the process and isolating the desired isomer and/or converting a free compound of formula I obtainable in accordance with the process or by another method, or a tautomer thereof, into a salt or converting a salt of a compound of formula I obtainable in accordance with the process or by another method, or a tautomer thereof, into the free compound of formula I or an isomer or tautomer thereof or into a different salt.

The present invention relates also to a process for the preparation of a compound of formula IIa, or a salt thereof, which comprises e) reacting a compound of formula

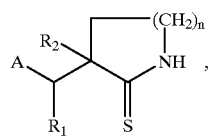

(IIIa)

wherein A, $R_1$, $R_2$ and n are as defined above for formula I, or a salt thereof, with a compound of formula:

Y—R₄ (V), wherein $R_4$ is $C_1$–$C_6$alkyl and Y is a leaving group, preferably in the presence of a base.

The compounds of formula IIa, the salts thereof and, where appropriate, the tautomers thereof and the salts of those tautomers are novel and the present invention relates also thereto.

The present invention relates further to a process for the preparation of a salt of formula IIb or, where appropriate, a tautomer thereof, which comprises f) reacting a compound of formula:

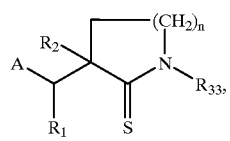

(IIIb)

wherein A, $R_1$, $R_2$ and n are as defined above for formula I and $R_{33}$ has the definitions given for $R_3$ in formula I with the exception of hydrogen, or a salt thereof, with a compound of formula (V), where appropriate in the presence of a base.

The salts of formula IIb and, where appropriate, the tautomers thereof are novel and the present invention relates also thereto.

The present invention relates further to a process for the preparation of a compound of formula III or, where appropriate, a tautomer thereof, in each case in free form or in salt form, which comprises g) reacting a compound of formula:

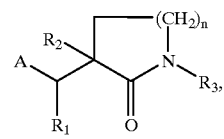

(VI)

wherein A, $R_1$, $R_2$, $R_3$ and n are as defined above for formula III, or a salt thereof, with a thionating agent.

The compounds of formula m and the tautomers thereof, in each case in free form or in salt form, are novel and the invention relates also thereto.

The present invention relates further to a process for the preparation of a compound of formula VI or, where appropriate, a tautomer thereof, in each case in free form or in salt form, which comprises h) reacting a compound of formula:

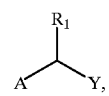

(VIII)

wherein A and $R_1$ are as defined above for formula I and Y is a leaving group, with a compound of formula:

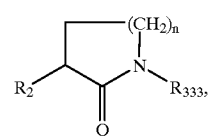

(VII)

wherein $R_2$ and n are as defined above for formula I and $R_{333}$ has the definitions given above for $R_3$ in formula I with the exception of hydrogen or is a protecting group, or a salt thereof, and where appropriate, if desired, i) converting a compound of formula:

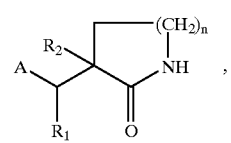

(VIa)

(obtainable by that process or by another method), wherein A, $R_1$, $R_2$ and n are as defined above for formula I, or a tautomer and/or a salt thereof, with a compound of formula:

Y—R₃₃ (IV), wherein $R_{33}$ is as defined for formula IIb and Y is a leaving group, into a compound of formula:

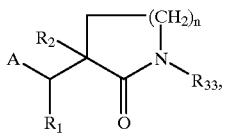

(VIb)

wherein A, $R_1$, $R_2$ and n are as defined above for formula I and $R_{33}$ has the definitions given for $R_3$ in formula IIb, or into a salt thereof.

The compounds of formula VI, in free form or in salt form, and, where appropriate, the tautomers thereof, in free form or in salt form, are novel and the invention relates also thereto.

The starting materials of formulae IV, V, VII and VIII referred to hereinbefore and hereinafter, which are used for the preparation of the compounds of formulae I, II, III and VI or, where appropriate, the tautomeric compounds thereof, in each case in free form or in salt form, are known or can be prepared in accordance with methods known per se.

The remarks made above in relation to the isomers and tautomers and/or the salts of compounds of formula I applies in analogous manner to the starting materials and intermediates of formulae II to VIII referred to hereinbefore and hereinafter as regards the possible tautomers and to the isomers and, where appropriate, the tautomers and/or the salts thereof.

The reactions of Variants a) to i) described hereinbefore and hereinafter are carried out in a manner known per se, for example in the absence or, customarily, the presence of a suitable solvent or diluent or of a mixture thereof, the reaction being carried out as required with cooling, at room temperature or with heating, for example in a temperature range of approximately from −120° C. to the boiling temperature of the reaction mixture, preferably from approximately −80° C. to approximately +150° C., and, if necessary, in a closed vessel, under pressure, in an inert gas atmosphere and/or under anhydrous conditions. Especially advantageous reaction conditions are to be found in the Examples.

Variants a, b and c):

The reactants can be reacted with one another as such, i.e. without the addition of a solvent or diluent, or, preferably, in the presence of a solvent or diluent. The following may be mentioned as examples of such solvents and diluents: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetra-chloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; alcohols, such as methanol, ethanol, propanol, isopropanol, butanol, ethylene glycol or glycerol; amides, such as N,N-dimethylformamide, N,N-diethylformarnide, N,N-dimethylacetamide, N-methylpyrrolidone or hexarnethylphosphoric acid triamide; nitriles, such as acetonitrile or propionitrile; and sulfoxides, such as dimethylsulfoxide.

Examples of suitable bases for facilitating the reaction with nitromethane or cyanamide are alkali metal or alkaline earth metal hydroxides, hydrides, amides, alkanolates, acetates, carbonates, dialkylamides or alkylsilylamides, or alkylamines, alkylenediamines, unsubstituted or N-alkylated, saturated or unsaturated cycloalkylamines, basic heterocycles, ammonium hydroxides and carbocyclic amines. There may be mentioned by way of example sodium hydroxide, hydride, amide, methanolate, acetate or carbonate, potassium tert-butanolate, hydroxide, carbonate or hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyl-trimethylammonium hydroxide and 1,5-diazabicyclo[5.4.0]undec-5-ene (DBU).

In a further variant, the reaction can be carried out with a metal salt of nitromethane or cyanamide. The alkali metal salts of nitromethane or cyanamide, especially the sodium salts, are especially suitable. The bases mentioned above are suitable for the preparation of the salts from free nitromethane or cyanamide.

Suitable as nitration agents for the reaction of a compound of formula II or III with ammonia and a nitration agent are the reagents customarily used for such reactions, such as nitric acid, $N_2O_3$, $N_2O_4$, $N_2O_5$, alkali metal nitrates, such as $KNO_3$ or $NaNO_3$, $AgNO_3$, alkyl nitrates, such as ethyl or butyl nitrate, and nitronium salts, such as $NO_2BF_4$ or $NO_2CF_3SO_3$, especially nitric acid.

In the nitration reactions according to the invention, it is preferable to add the customary acids, that is to say, for example, sulfuric acid, perchloric acid, methanesulfonic acid, trifluoromethanesulfonic acid or phosphoric acid. Special preference is given, however, to a process in which nitric acid is used for the nitration.

A further preferred form of Variant b) comprises adding to the reaction mixture a precipitating agent for the anion, such as silver carbonate or barium chloride.

The reaction is advantageously carried out in a temperature range from approximately 0° C. to approximately +200° C., preferably from approximately +10° C. to approximately +140° C., and in many cases in the range from room temperature to the reflux temperature of the reaction mixture.

Variant d:

The reactants can be reacted with one another as such, i.e. without the addition of a solvent or diluent, for example in the melt. Generally, however, the addition of an inert solvent or diluent or of a mixture thereof is advantageous. Examples of such solvents or diluents are, for example, the same as those mentioned for Variants a) to c).

Suitable leaving groups Y in the compounds of formulae IV, V and VII are, for example, hydroxy, $C_1$–$C_8$alkoxy, halo-$C_1$–$C_8$alkoxy, $C_1$–$C_8$alkanoyloxy, mercapto, $C_1$–$C_8$alkylthio, halo-$C_1$–$C_8$alkylthio, $C_1$–$C_8$alkanesulfonyloxy, halo-$C_1$–$C_8$alkanesulfonyloxy, benzenesulfonyloxy, toluenesulfonyloxy, sulfate and halogen, especially toluenesulfonyloxy, trifluoromethylsulfonyloxy, sulfate and halogen, more especially sulfate, chlorine, bromine and iodine.

Suitable bases for facilitating the H-Y removal are, for example, those of the type indicated for Variants a) to c).

The reaction is advantageously carried out in a temperature range of from approximately −100° C. to approximately +180° C., preferably from approximately −100° C. to approximately +130° C., and in many cases in the range from room temperature to the reflux temperature of the reaction mixture.

Variants e and f):

The reactants can be reacted with one another as such, i.e. without the addition of a solvent or diluent, for example in the melt. Generally, however, the addition of an inert solvent or diluent or of a mixture thereof is advantageous. Suitable solvents or diluents. are, for example, those of the type mentioned for Variants a) to c).

The reaction is advantageously carried out in a temperature range of from approximately −20° C. to approximately +160° C., preferably from 0° C. to +120° C., and in many cases at the reflux temperature of the reaction mixture.

Suitable bases for facilitating the H-Y removal are, for example, those of the type indicated for Variant a).

Suitable leaving groups Y in the compounds of formula V are, for example, those of the type indicated for Variant d).

Variant g):

The reactants can be reacted with one another as such, i.e. without the addition of a solvent or diluent, for example in the melt. Generally, however, the addition of an inert solvent or diluent or of a mixture thereof is advantageous. Suitable solvents or diluents are, for example, those of the type mentioned for Variants a) to c).

The reaction is preferably carried out in a temperature range of from 0° C. to +200° C., preferably at from room temperature to +150° C.

Suitable thionating agents are, for example, O,O-diethyldithiophosphoric acid, $B_2S_3$, $B_2S_5$, phosphorus pentasulfide and Lawesson's reagent [2,4-bis(4methoxyphenyl)-1,3-dithia-2,4-diphosphetane 2,4-disulfide].

Variant h):

The reactants can be reacted with one another as such, i.e. without the addition of a solvent or diluent, for example in the melt Generally, however, the addition of an inert solvent or diluent or of a mixture thereof is advantageous. Suitable solvents or diluents are, for example, those of the type mentioned for Variants a) to c).

The reaction is preferably carried out in a temperature range of from −120° C. to +100° C., preferably at from −80° C. to +60° C., and preferably in the presence of a base. Suitable bases for the H-Y removal are, for example, those of the type mentioned for synthesis Variants a) to c). Suitable leaving groups Y are the groups indicated for synthesis Variant d), especially halogen.

When $R_3$ in the compound of formula VI to be prepared is hydrogen, $R_{333}$ in the compound of formula VII must be a protecting group. Suitable protecting groups are those that are customarily used, such as acyl, trialkylsilyl, such as trimethylsilyl, or alkyl, such as tert-butyl, which can be removed again, if necessary, in a further synthesis step.

Variant i):

The same conditions as those mentioned for Variant d) apply.

Salts of compounds of formulae I, II, III and VI can be prepared in a manner known per se. For example, acid addition salts are obtained by treatment with a suitable acid or a suitable ion exchange reagent, and salts with bases are obtained by treatment with a suitable base or a suitable ion exchange reagent.

Salts of compounds of formulae I, II, III and VI can be converted into the free compounds of formulae I, II, III and VI in customary manner acid addition salts, for example, by treatment with a suitable basic agent or a suitable ion exchange reagent, and salts with bases, for example, by treatment with a suitable acid or a suitable ion exchange reagent.

Salts of compounds of formulae I, II, III and VI can be converted into different salts of compounds of formulae I, II, III and VI in a manner known per se: acid addition salts, for example, can be converted into different acid addition salts, for example by treatment of a salt of an inorganic acid, such as a hydrochloride, with a suitable metal salt, such as a sodium, barium or silver salt, of an acid, for example with silver acetate, in a suitable solvent in which an inorganic salt being formed, for example silver chloride, is insoluble and therefore is eliminated from the reaction mixture.

Depending upon the procedure and the reaction conditions, compounds of formulae I, II, III and VI having salt-forming properties can be obtained in free form or in the form of salts.

The compounds of formulae I, II, III and VI and, where appropriate, their tautomers, in each case in free form or in salt form, may be in the form of one of the possible isomers or as a mixture thereof, for example according to the number of asymmetric carbon atoms occurring in the molecule and the absolute and relative configuration thereof and/or according to the configuration of non-aromatic double bonds occurring in the molecule, they may be in the form of pure isomers, such as antipodes and/or diastereoisomers, or in the form of mixtures of isomers, such as mixtures of enantiomers, for example racemates, mixtures of diastereoisomers or mixtures of racemates; the invention relates both to the pure isomers and to all possible mixtures of isomers and this is to be understood hereinbefore and hereinafter, even when stereochemical details are not specifically mentioned in each case.

Mixtures of diastereoisomers and mixtures of racemates of compounds of formulae I, II, III and VI, or their salts, that are obtainable in accordance with the process, depending upon the starting materials and procedures chosen, or by another method, can be separated into the pure diastereoisomers or racemates in known manner on the basis of the physicochemical differences between the constituents, for example by fractional crystallisafion, distillation and/or chromatography.

Mixtures of enantiomers, such as racemates, so obtainable can be separated into the optical antipodes by known methods, for example by recrystallisation from an optically active solvent, by chromatography on chiral adsorbents, for example high-pressure liquid chromatography (HPLC) on acetyl cellulose, with the aid of suitable microorganisms, by cleavage with specific immobilised enzymes, via the formation of inclusion compounds, for example using chiral crown ethers, in which case only one enantiomer is complexed, or by conversion into diastereoisomeric salts, for example by reaction of a basic end product racemate with an optically active acid, such as a carboxylic acid, for example camphoric, tartaric or malic acid, or sulfonic acid, for example camphorsulfonic acid, and separation of the resulting mixture of diastereoisomers, for example on the basis of their different solubilities by fractional crystallisation, into the diastereoisomers from which the desired enantiomer can be freed by the action of suitable, for example basic, agents.

Apart from by the separation of corresponding mixtures of isomers, it is possible according to the invention to obtain pure diastereoisomers or enantiomers also by generally known methods of diastereoselective or enantioselective synthesis, for example by carrying out the process according to the invention with starting materials having suitable stereochemistry.

It is advantageous to isolate or synthesise the biologically more active isomer, for example enantiomer or diastereoisomer, or mixture of isomers, for example mixture of enantiomers or mixture of diastereoisomers, insofar as the individual components have different biological activity.

The compounds of formulae I, II, III and VI and their salts can also be obtained in the form of their hydrates and/or may include other solvents, for example solvents that may be used for the crystallisation of compounds in solid form.

The invention relates to all those forms of the process according to which a compound obtainable as starting material or intermediate at any stage of the process is used as starting material and all or some of the remaining steps are carried out, or a starting material is used in the form of a derivative or a salt and/or its racemates or antipodes o; especially, is formed under the reaction conditions.

Compounds of formula I obtainable in accordance with the process or by another can be converted in a manner known per se into different compounds of formula I In particular, for example, compounds of formulae I, II, III, VI and VII having heterocyclic radicals A that contain a nitrogen atom as hetero atom, can be converted by oxidation into the desired N-oxides, or the radicals A can be halogenated.

In the process of the present invention there are preferably used those starting materials and intermediates, in each case in free form or in salt form, which result in the compounds of formula I described at the beginning as being especially valuable, or their salts.

The invention relates especially to the preparation processes described in Examples P1 to P19.

In the area of pest control, the compounds of formula I according to the invention are valuable preventive and/or curative active ingredients having a very advantageous biocidal spectrum even at low rates of concentration, while being well tolerated by warm-blooded animals, fish and plants. The compounds of the invention are effective against all or individual development stages of normally sensitive animal pests, but also of resistant animal pests, such as insects. The insecticidal action of the compounds of the invention may manifest itself directly, i.e. in the mortality of the pests, which occurs immediately or only after some time, for example during moulting, or indirectly, for example in reduced oviposition and/or hatching rate, good activity corresponding to a mortality of at least 50 to 60%.

The mentioned animal pests include, for example:

of the order Lepidoptera, for example, Acleris spp., Adoxophyes spp., Aegeria spp., Agrotis spp., Alabama argillaceae, Amylois spp., Anticarsia gemmatalis, Archips spp., Argyrotaenia spp., Autographa spp., Busseola fusca, Cadra cautella, Carposina nipponensis, Chilo spp., Choristoneura spp., Clysia ambiguella, Cnaphalocrocis spp., Cnephasia spp., Cochylis spp., Coleophora spp., Crocidolomia binotalis, Cryptophlebia leucotreta, Cydia spp., Diatraea spp., Diparopsis castanea, Earias spp., Ephestia spp., Eucosma spp., Eupoecilia ambiguella, Euproctis spp., Euxoa spp., Grapholita spp., Hedya nubiferana, Heliotnis spp., Hellula undalis, Hyphantria cunea, Keiferia lycopersicella, Leucoptera scitella, Lithocollethis spp., Lobesia botrana, Lymantria spp., Lyonetia spp., Malacosoma spp., Mamestra brassicae, Manduca sexta, Operophtera spp., Ostrinia nubilalis, Pammene spp., Pandemis spp., Panolis flammea, Pectinophora gossypiella, Phthorimaea operculella, Pieris rapae, Pieris spp., Plutella xylostella, Prays spp., Scirpophaga spp., Sesamia spp., Sparganothis spp., Spodoptera spp., Synanthedon spp., Thaumetopoea spp., Tortrix spp., Trichoplusia ni and Yponomeuta spp.;

of the order Coleoptera, for example, Agriotes spp., Anthonomus spp., Atomaria linearis, Chaetocnema tibialis, Cosmopolites spp., Curculio spp., Dermestes spp., Diabrotica spp., Epilachna spp., Eremnus spp., Leptinotarsa decemlineata, Lissorhoptrus spp., Melolontha spp., Orycaephilus spp., Otiorhynchus spp., Phlyctinus spp., Popillia spp., Psylliodes spp., Rhizopertia spp., Scarabeidae, Sitophilus spp., Sitotroga spp., Tenebrio spp., Tribolium spp. and Trogoderma spp.;

of the order Orthoptera, for example, Blatta spp., Blattella spp., Gryllotalpa spp., Leucophaea maderae, Locusta spp., Periplaneta spp. and Schistocerca spp.;

of the order Isoptera, for example, Reticulitermes spp.;

of the order Psocoptera, for example, Liposcelis spp.;

of the order Anoplura, for example, Haematopinus spp., Linognathus spp., Pediculus spp., Pemphigus spp. and Phylloxera spp.;

of the order Mallophaga, for example, Damalinea spp. and Trichodectes spp.;

of the order Thysanoptera, for example, Frankliniella spp., Hercinothrips spp., Taeniothrips spp., Thrips palmi, Thrips tabaci and Scirtothrips aurantii;

of the order Heteroptera, for example, Cimex spp., Distantiella theobroma, Dysdercus spp., Euchistus spp., Eurygaster spp., Leptocorisa spp., Nezara spp., Piesma spp., Rhodnius spp., Sahlbergella singularis, Scotinophara spp. and Triatoma spp.;

of the order Homoptera, for example, Aleurothrixus floccosus, Aleyrodes brassicae, Aonidiella spp., Aphididae, Aphis spp., Aspidiotus spp., Bemisia tabaci, Ceroplaster spp., Chrysomphalus aonidium, Chrysomphalus dictyospermi, Coccus hesperidum, Empoasca spp., Eriosoma larigerum, Erythroneura spp., Gascardia spp., Laodelphax spp., Lecanium corni, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., Pulvinaria aethiopica, Quadraspidiotus spp., Rhopalosiphum spp., Saissetia spp., Scaphoideus spp., Schizaphis spp., Sitobion spp., Trialeurodes vaporariorum, Trioza erytreae and Unaspis citri;

of the order Hymenoptera, for example, Acromyrmex, Atta spp., Cephus spp., Diprion spp., Diprionidae, Gilpinia polytoma, Hoplocampa spp., Lasius spp., Monomorium pharaonis, Neodiprion spp., Solenopsis spp. and Vespa spp.;

of the order Diptera, for example, Aedes spp., Antherigona soccata, Bibio hortulanus, Calliphora erythrocephala, Ceratitis spp., Chrysomyia spp., Culex spp., Cuterebra spp., Dacus spp., Drosophila melanogaster, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp.,. Oscinella frit, Pegomyia hyoscyami, Phorbia spp., Rhagoletis pomonella, Sciara spp., Stomoxys spp., Tabanus spp., Tannia spp. and Tipula spp.;

of the order Siphonaptera, for example Ceratophyllus spp. and Xenopsylla cheopis, and of the order Thysanura, for example, Lepisma saccharina.

With the compounds according to the invention it is possible to control, i.e. to inhibit or destroy, pests of the mentioned type occurring especially on plants, especially on useful plants and ornamentals in agriculture, in horticulture and in forestry, or on parts of such plants, such as the fruit, blossom, leaves, stems, tubers or roots, while some of the parts of the plants which grow later are also protected against those pests.

Target crops are especially cereals, such as wheat, barley, rye, oats, rice, maize and sorghum; beet, such as sugar beet and fodder beet; fruit, such as pomes, stone fruit and soft fruit, such as apples, pears, plums, peaches, almonds, cherries, or berries, for example strawberries, raspberries or blackberries; leguminous plants, such as beans, lentils, peas and soybeans; oil plants, such as rape, mustard, poppy, olives, sunflowers, coconut, castor oil plants, cocoa beans and groundnuts; cucumber plants, such as marrows, cucumbers and melons; fibre plants, such as cotton, flax, hemp and jute; citrus fruit, such as oranges, lemons, grapefruit and mandarins; vegetables, such as spinach, lettuce, asparagus, cabbages, carrots, onions, tomatoes, potatoes and paprika; lauraceae, such as avocados, cinnamon and camphor; and tobacco, nuts, coffee, aubergines, sugar cane, tea, pepper, vines, hops, bananas and natural rubber plants, as well as ornamentals.

The compounds of the invention are suitable especially for controlling Aphis craccivora, Bemisia tabaci, Heliothis virescens, Myzus persicae, Nephotettix cincticeps and Nilaparvata lugens in vegetable, fruit, rice and soybean crops.

Further areas of use of the compounds according to the invention are the protection of stored goods and stocks and materials, and also in the hygiene sector, especially the protection of domestic animals and productive livestock against pests of the mentioned type.

The invention therefore relates also to pesticides, such as emulsifiable concentrates, suspension concentrates, directly sprayable or dilutable solutions, coatable pastes, dilute emulsions, wettable powders, soluble powders, dispersible powders, wettable powders, dusts, granules or encapsulations in polymer substances, comprising—at least—one of the compounds of the invention, the type of formulation being chosen in accordance with the intended objectives and prevailing circumstances.

The active ingredient is used in those compositions in pure form, a solid active ingredient, for example, in a specific particle size, or preferably together with—at least—one of the adjuvants customary in formulation technology, such as extenders, for example solvents or solid carriers, or surface-active compounds (surfactants).

Suitable solvents are, for example: optionally partially hydrogenated aromatic hydrocarbons, preferably the fractions of alkylbenzenes containing 8 to 12 carbon atoms, such as xylene mixtures, alkylated naphthalenes or tetrahydronaphthalene, aliphatic or cycloaliphatic hydrocarbons, such as paraffins or cyclohexane, alcohols, such as ethanol, propanol or butanol, glycols and their ethers and esters, such as propylene glycol, dipropylene glycol ether, ethylene glycol or ethylene glycol monomethyl or monoethyl ether, ketones, such as cyclohexanone, isophorone or diacetone alcohol, strongly polar solvents, such as N-methylpyrrolid-2-one, dimethyl sulfoxide or N,N-dimethylformamide, water, vegetable oils or epoxidised vegetable oils, such as rape oil, castor oil, coconut oil or soybean oil or epoxidised rape oil, castor oil, coconut oil or soybean oil, and silicone oils.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, such as pumice, broken brick, sepiolite or bentonite; and suitable nonsorbent carriers are calcite or sand. In addition, a great number of granulated materials of inorganic or organic nature can be used, especially dolomite or pulverised plant residues.

Depending on the nature of the compound to be formulated, suitable surface-active compounds are non-ionic, cationic and/or anionic surfactants or mixtures of surfactants having good emulsifying, dispersing and wetting properties. The surfactants listed below are to be regarded merely as examples; many more surfactants customarily employed in formulation technology and suitable for use according to the invention are described in the relevant literature.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol uniL Representative examples of non-ionic surfactants are nonylphenol polyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates. An example is stearyltrimethylammonium chloride.

Both water-soluble soaps and water-soluble synthetic surface-active compounds are suitable anionic surfactants. Suitable soaps are the alkali metal salts, alkaline earth metal salts and unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tall oil; mention may also be made of fatty acid methyltaurin salts. More frequently, however, synthetic surfactants are used, especially fatty sulfonates, fatty sulfates, sulfonated benzimidazole derivatives or alkylarylsulfonates. The fatty sulfonates or sulfates are usually in the form of alkali metal salts, allaine earth metal salts or unsubstituted or substituted ammonium salts and generally contain a $C_8$–$C_{22}$alkyl radical, which also includes the alkyl moiety of acyl radicals; there may be mentioned by way of example the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing approximately 8 to 22 carbon atoms. Examples of alkylarylsulfonates are the sodium, calcium or triethanolammonium salts of dodecylbenzenesulfonic acid, dibutylnaphthalenesulfonic acid or of a condensate of naphthalenesulfonic acid and formaldehyde. Also suitable are corresponding phosphates, e.g. salts of the phosphoric acid ester of an adduct of p-nonylphenol with 4 to 14 mol of ethylene oxide, or phospholipids.

The compositions usually comprise 0.1 to 99%, preferably 0.1 to 95%, of active ingredient, and 1 to 99.9%, preferably 5 to 99.9%, of—at least—one solid or liquid adjuvant, it generally being possible for 0 to 25%, preferably 0.1 to 20%, of the composition to be surfactants (in each case percentages are by weight). Whereas commercial products will preferably be formulated as concentrates, the end user will normally employ dilute formulations which have considerably lower active ingredient concentrations. Preferred formulations have especially the following composition (throughout, percentages are by weight):

Emulsifiable concentrates:
    active ingredient: 1 to 90%, preferably 5 to 50%
    surfactant: 1 to 30%, preferably 10 to 50%
    solvent: 5 to 98%, preferably 70 to 85%
Dusts:
    active ingredient: 0.1 to 10%, preferably 0.1 to 5%
    solid carrier: 99.9 to 90%, preferably 99.9 to 99%
Suspension concentrates:
    active ingredient: 5 to 75%, preferably 10 to 50%
    water: 94 to 24%, preferably 88 to 30%
    surfactant: 1 to 40%, preferably 2 to 30%
Wettable powders:
    active ingredient: 0.5 to 90%, preferably 1 to 80%
    surfactant: 0.5 to 20%, preferably 1 to 15%
    solid carrier: 5 to 99%, preferably 15 to 98%
Granules:
    active ingredient: 0.5 to 30%, preferably 3 to 15%
    solid carrier: 99.5 to 70%, preferably 97 to 85%

The activity of the compositions according to the invention can be substantially broadened and adapted to prevailing circumstances by the addition of other insecticidal active ingredients. Examples of suitable additional active ingredients include representatives of the following classes of compounds: organophosphorus compounds, nitrophenols and derivatives, formamidines, ureas, carbamates, pyrethroids, chlorinated hydrocarbons, and Bacillus thuringiensis preparations. The compositions according to the invention may also comprise further solid or liquid adjuvants, such as stabilisers, for example vegetable oils or epoxidised vegetable oils (e.g. epoxidised coconut oil, rape oil or soybean oil), antifoams, for example silicone oil, preservatives, viscosity regulators, binders and/or tackifiers, as well as fertilisers or other active ingredients for obtaining special effects, for example acaricides, bactericides, fungicides, nematicides, molluscicides or selective herbicides.

The compositions according to the invention are prepared in known manner, in the absence of adjuvants, for example by grinding, sieving and/or compressing a solid active ingredient or mixture of active ingredients, for example to a specific particle size, and in the presence of at least one adjuvant, for example by intimately mixing and/or grinding the active ingredient or mixture of active ingredients with the adjuvant(s). The invention relates also to those processes for the preparation of the compositions according to the invention and to the use of the compounds of formula I for the preparation of those compositions.

The invention relates also to the methods of application of the compositions, i.e. the methods of controlling pests of the mentioned type, such as spraying, atomising, dusting, coating, dressing, scattering or pouring, which are selected in accordance with the intended objectives and prevailing circumstances, and to the use of the compositions for controlling pests of the mentioned type. Typical rates of concentration are from 0.1 to 1000 ppm, preferably from 0.1 to 500 ppm, of active ingredient The rates of application per hectare are generally from 1 to 2000 g of active ingredient per hectare, especially from 10 to 1000 g/ha, preferably from 20 to 600 g/ha.

A preferred method of application in the area of plant protection is application to the foliage of the plants (foliar application), the number of applications and the rate of application depending on the risk of infestation by the pest in question. However, the active ingredient can also penetrate the plants through the roots (systemic action) if the locus of the plants is impregnated with a liquid formulation or if the active ingredient is incorporated in solid form into the locus of the plants, for example into the soil, e.g. in granular form (soil application). In paddy rice crops, such granules may be applied in metered amounts to the flooded rice field.

The compositions according to the invention are also suitable for protecting plant propagation material, e.g. seed material, such as fruit, tubers or grains, or plant cuttings, from animal pests. The propagation material can be treated with the formulation before planting: seed, for example, can be dressed before being sown. The compounds of the invention can also be applied to grains (coating), either by impregnating the grains with a liquid formulation or by coating them with a solid formulation. The formulation can also be applied to the planting site when the propagation material is being planted, for example to the seed furrow during sowing. The invention relates also to those methods of treating plant propagation material and to the plant propagation material thus treated.

The following Examples are intended tog illustrate the invention and do not limit the invention. Ratios of solvents are given in parts by volume.

PREPARATION EXAMPLES

Example P1

3-(2-Chloropyrid-5-yl-methyl)-pyrrolid-2-one

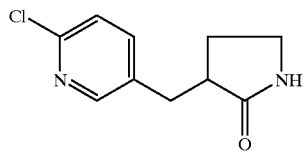

Under a nitrogen atmosphere at a temperature of from −78° C. to −60° C., 180 ml of a 1.5 molar solution of lithium diisopropylamide (LDA) in cyclohexane are added dropwise to 31.4 g of N-trimethylsilylpylrolid-2-one in 150 ml of tetrahydrofuran CIF) and the reaction mixture is stirred at the same temperature for a further one hour. Then, at from −78° C. to −60° C., 25.5 g of 2-chloro-5-chloromethylpyridine in 40 ml of THF are added, and the mixture is stirred for a further 16 hours at that temperature and then for a further three hours at room temperature. The reaction mixture is poured onto a mixture of ice/water and extracted with ethyl acetate, and the organic phase is separated off. The ethyl acetate phase is dried over sodium sulfate and concentrated to dryness by evaporation in vacuo. The residue is purified on silica gel using ethyl acetatelhexane (7:1) as eluant The title compound having a melting point of 117–118° C. (compound 1.3) is obtained.

Example P2

3-(2-Chloropyrid-5-yl-methyl)-1-methyl-pyrrolid-2-one

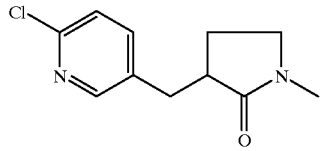

Under an argon atmosphere at a temperature of from −78° C. to −60° C., 150 ml of a 1.5 molar solution of lithium diisopropylamide (LDA) in cyclohexane are added dropwise in the course of one hour to 20 g of N-methylpyrrolid-2-one in 50 ml of tetrahydrofuran (THF) and the reaction mixture is stirred at the same temperature for a further one hour. Then, at from −78° C. to −60° C., 25.0 g of 2-chloro-5-(chloromethyl)-pyridine in 40 ml of THF are added, and the mixture is stirred for a further 6 hours at that temperature and then for a further 6 hours at 0° C. 15 ml of methanol are added and the reaction mixture is then poured onto a mixture of ice/water and extracted with ethyl acetate, and the organic phase is separated off. The ethyl acetate phase is dried over magnesium sulfate and concentrated to dryness by evaporation in vacuo. The residue is purified on silica gel using ethyl acetate/hexane (7:1) as eluant The title compound (compound 1.4) is obtained in the form of a colourless oil.

Example P3

The other compounds listed in Table 1 can be prepared in a manner analogous to that described in Examples P1 and P2.

TABLE 1

Compounds of the formula:

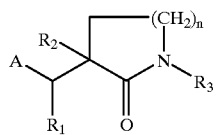

| Comp. No. | A | n | $R_1$ | $R_2$ | $R_3$ | Phys. data |
|---|---|---|---|---|---|---|
| 1.1 | pyrid-3-yl | 1 | H | H | H | |
| 1.2 | pyrid-3-yl | 1 | H | H | $CH_3$ | |
| 1.3 | 2-Cl-pyrid-5-yl | 1 | H | H | H | m.p. 117–118° C. |
| 1.4 | 2-Cl-pyrid-5-yl | 1 | H | H | $CH_3$ | oil |
| 1.5 | 2-Cl-thiazol-5-yl | 1 | H | H | H | |
| 1.6 | 2-Cl-thiazol-5-yl | 1 | H | H | $CH_3$ | |
| 1.7 | pyrid-3-yl | 2 | H | H | H | |
| 1.8 | pyrid-3-yl | 2 | H | H | $CH_3$ | |
| 1.9 | 2-Cl-pyrid-5-yl | 2 | H | H | H | m.p. 129–130° C. |
| 1.10 | 2-Cl-pyrid-5-yl | 2 | H | H | $CH_3$ | |
| 1.11 | 2-Cl-thiazol-5-yl | 2 | H | H | H | |
| 1.12 | 2-Cl-thiazol-5-yl | 2 | H | H | $CH_3$ | |

Example P4

3-(2-Chloropyrid-5-yl-methyl)-pyrrolide-2-thione

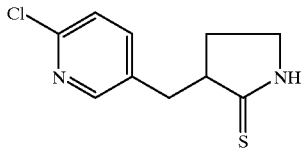

A mixture of 1.0 g of 3-(2-chloropyrid-5-yl-methyl)-pyrrolid-2-one and 0.96 g of Lawesson's reagent [2,4-bis (4-methoxyphenyl)-1,3-dithia-2,4-diphosphetane 2,4-disulfide] in 15 ml of toluene is boiled at reflux for 15 minutes. After removal of the solvent, the residue is purified on silica gel using ethyl acetate/hexane (6:1) as eluant. The title compound having a melting point of 151–152° C. (compound 2.3) is obtained.

Example P5

3-(2-Chloropyrid-5-yl-methyl)-1-methyl-pyrrolide-2-thione

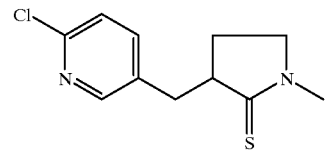

A mixture of 10 g of 3-(2-chloropyrid-5-yl-methyl)-1-methyl-pyrrolid-2-one and 9 g of Lawesson's reagent in 40 ml of toluene is boiled at reflux for 15 minutes. After removal of the solvent, the residue is purified on silica gel using ethyl acetate/hexane (6:1) as eluant The title compound is obtained in the form of a yellowish solid having a melting point of 44–47° C. (compound 2.4).

Example P6

The other compounds listed in Table 2 can be prepared in a manner analogous to that described in Examples P4 and P5.

TABLE 2

Compounds of the formula:

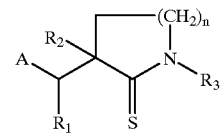

| Comp. No. | A | n | $R_1$ | $R_2$ | $R_3$ | Phys. data |
|---|---|---|---|---|---|---|
| 2.1 | pyrid-3-yl | 1 | H | H | H | |
| 2.2 | pyrid-3-yl | 1 | H | H | $CH_3$ | |
| 2.3 | 2-Cl-pyrid-5-yl | 1 | H | H | H | m.p. 151–152° C. |
| 2.4 | 2-Cl-pyrid-5-yl | 1 | H | H | $CH_3$ | m.p. 44–47° C. |
| 2.5 | 2-Cl-thiazol-5-yl | 1 | H | H | H | |
| 2.6 | 2-Cl-thiazol-5-yl | 1 | H | H | $CH_3$ | |
| 2.7 | pyrid-3-yl | 2 | H | H | H | |
| 2.8 | pyrid-3-yl | 2 | H | H | $CH_3$ | |

TABLE 2-continued

Compounds of the formula:

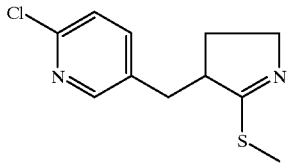

| Comp. No. | A | n | $R_1$ | $R_2$ | $R_3$ | Phys. data |
|---|---|---|---|---|---|---|
| 2.9 | 2-Cl-pyrid-5-yl | 2 | H | H | H | m.p. 162–163° C. |
| 2.10 | 2-Cl-pyrid-5-yl | 2 | H | H | $CH_3$ | |
| 2.11 | 2-Cl-thiazol-5-yl | 2 | H | H | H | |
| 2.12 | 2-Cl-thiazol-5-yl | 2 | H | H | $CH_3$ | |

Example P7

3-(2-Chloropyrid-5-yl-methyl)-2-methylthio-1-azacyclopentene 0.6 g of 3-(2-chloropyrid-5-yl-methyl)-pyrrolide-2-thione are added to a mixture of 0.1 g of sodium hydride (50% in oil) and 10 ml of dimethylformamide. The mixture is stirred for 20 minutes at room temperature and then 0.38 g of methyl iodide is added. The reaction mixture is stirred for a further 30 minutes at room temperature, poured onto ice-water and extracted with ethyl acetate. The organic phase is dried over magnesium sulfate and concentrated to dryness by evaporation in vacuo. The title compound is obtained in the form of an oil (compound 3.2).

Example P8

The other compounds listed in Table 3 can be prepared in a manner analogous to that described in Example P7.

TABLE 3

Compounds of the formula:

| Comp. No. | A | n | $R_1$ | $R_2$ | $R_4$ | Phys. data |
|---|---|---|---|---|---|---|
| 3.1 | pyrid-3-yl | 1 | H | H | $CH_3$ | |
| 3.2 | 2-Cl-pyrid-5-yl | 1 | H | H | $CH_3$ | oil |
| 3.3 | 2-Cl-pyrid-5-yl | 1 | H | H | $C_2H_5$ | |
| 3.4 | 2-Cl-thiazol-5-yl | 1 | H | H | $CH_3$ | |
| 3.5 | pyrid-3-yl | 2 | H | H | $CH_3$ | |
| 3.6 | 2-Cl-pyrid-5-yl | 2 | H | H | $CH_3$ | oil |
| 3.7 | 2-Cl-pyrid-5-yl | 2 | H | H | $C_2H_5$ | |
| 3.8 | 2-Cl-thiazol-5-yl | 2 | H | H | $CH_3$ | |

Example P9

3-(2-Chloropyrid-5-yl-methyl)-1-methyl-2-methylthio-1-azacyclopentenylium iodide

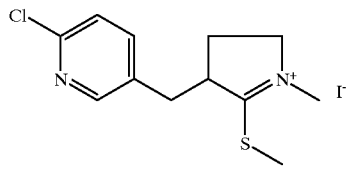

A mixture of 5.0 g of 3-(2-chloropyrid-5-yl-methyl)-1-methyl-pyrrolide-2-thione and 3 g of methyl iodide is maintained at 40° C. for four hours without stirring. The excess methyl iodide is removed in vacuo. The title compound having a melting point of 144–147° C. (compound 4.2) is obtained.

Example P10

The other compounds listed in Table 4 can be prepared in a manner analogous to that described in Example P9.

TABLE 4

Compounds of the formula:

| Comp. No. | A | n | $R_1$ | $R_2$ | $R_3$ | $R_4$ | Y | Phys. data |
|---|---|---|---|---|---|---|---|---|
| 4.1 | pyrid-3-yl | 1 | H | H | $CH_3$ | $CH_3$ | I | |
| 4.2 | 2-Cl-pyrid-5-yl | 1 | H | H | $CH_3$ | $CH_3$ | I | m.p. 144–147° C. |
| 4.3 | 2-Cl-pyrid-5-yl | 1 | H | H | $CH_3$ | $C_2H_5$ | I | |
| 4.4 | 2-Cl-thiazol-5-yl | 1 | H | H | $CH_3$ | $CH_3$ | I | |
| 4.5 | pyrid-3-yl | 2 | H | H | $CH_3$ | $CH_3$ | I | |
| 4.6 | 2-Cl-pyrid-5-yl | 2 | H | H | $CH_3$ | $CH_3$ | I | |
| 4.7 | 2-Cl-pyrid-5-yl | 2 | H | H | $CH_3$ | $C_2H_5$ | I | |
| 4.8 | 2-Cl-thiazol-5-yl | 2 | H | H | $CH_3$ | $CH_3$ | I | |

Example P11

3-(2-Chloropyrid-5-yl-methyl)2-nitromethylidene-pyrrolidine

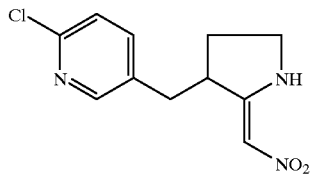

A mixture of 0.4 g of 3-(2-chloropyrid-5-yl-methyl)-2-methylthio-1-azacyclopent-1-ene and 10 ml of nitromethane is stirred at reflux temperature for five days. The mixture is concentrated by evaporation in vacuo and the residue is purified on silica gel using dichloromethane/methanol (95:5) as eluant. The title compound having a melting point of 159–160° C. is obtained (compound 5.3).

Example P12

3-(2-Chloropyrid-5-yl-methyl)-1methyl-2-nitromethylidene-pyrrolidine

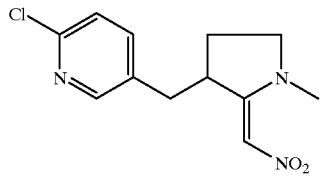

A mixture of 4.0 g of 3-(2-chloropyrid-5-yl-methyl)-1-methyl-2-methylthio-1-azacyclopent-1-enylium iodide, 4.0 g of potassium carbonate and 40 ml of nitromethane is heated at 100° C. for 15 minutes. The mixture is concentrated to dryness by evaporation and the residue is chromatographed on silica gel using ethyl acetate as eluant. The title compound having a melting point of 141–142° C. is obtained (compound 5.4).

Example P13

3-(2-Chloropyrid-5-yl-methyl) l-methyl-2-nitromethylidene-pyrrolidine

A mixture of 3-(2-chloropyrid-5-yl-methyl)-1-methyl-pyrrolide-2-thione, 0.12 g of silver carbonate and 3 ml of nitromethane is stirred at reflux for one hour. The mixture is concentrated by, evaporation in vacuo and the crude product is chromatographed on silica gel with ethyl acetate. The title compound having a melting point of 141–142° C. (compound 5.4) is obtained.

Example P14

3-(2-Chloropyrid-5-yl-methyl)-1-ethyl-2-nitromethylidene-pyrrolidine

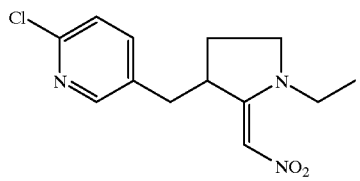

A mixture of 0.5 g of 3-(2-chloropyrid-5-yl-methyl)-2-nitromethylidene-pyrrolidine, 0.3 g of ethyl iodide and 0.27 g of potassium carbonate in 3 ml of dimethylformamide is stirred at room temperature for 18 hours. The reaction mixture is poured onto water and extracted with diethyl ether. The ether phase is dried over magnesium sulfate and concentrated by evaporation in vacuo. The residue is chromatographed on silica gel with ethyl acetate/hexane (2:1). The title compound having a melting point of 129–131° C. (compound 5.5) is obtained.

Example P15

The other compounds listed in Table 5 can be prepared in a manner analogous to that described in Examples P11 to P14.

TABLE 5

Compounds of the formula:

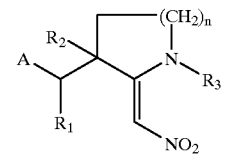

| Comp. No. | A | n | $R_1$ | R | $R_3$ | m.p. (° C.) |
|---|---|---|---|---|---|---|
| 5.1 | pyrid-3-yl | 1 | H | H | H | |
| 5.2 | pyrid-3-yl | 1 | H | H | $CH_3$ | |
| 5.3 | 2-Cl-pyrid-5-yl | 1 | H | H | H | 159–161° C. |
| 5.4 | 2-Cl-pyrid-5-yl | 1 | H | H | $CH_3$ | 141–142° C. |
| 5.5 | 2-Cl-pyrid-5-yl | 1 | H | H | $C_2H_5$ | 129–131° C. |
| 5.6 | 2-Cl-pyrid-5-yl | 1 | H | H | $C_3H_7$-n | 128–129° C. |
| 5.7 | 2-Cl-pyrid-5-yl | 1 | H | H | $CH_2CH=CH_2$ | 116–117° C. |
| 5.8 | 2-Cl-pyrid-5-yl | 1 | H | H | $CH_2C\equiv CH$ | |
| 5.9 | 2-Cl-pyrid-5-yl | 1 | H | H | $C_4H_9$-n | |
| 5.10 | 2-Cl-thiazol-5-yl | 1 | H | H | H | |
| 5.11 | 2-Cl-thiazol-5-yl | 1 | H | H | $CH_3$ | |
| 5.12 | 2-Cl-pyrid-5-yl | 1 | $CH_3$ | H | H | |
| 5.13 | 2-Cl-pyrid-5-yl | 1 | H | $CH_3$ | H | |
| 5.14 | pyrid-3-yl | 2 | H | H | H | |
| 5.15 | pyrid-3-yl | 2 | H | H | $CH_3$ | |
| 5.16 | 2-Cl-pyrid-5-yl | 2 | H | H | H | 179–181° C. |
| 5.17 | 2-Cl-pyrid-5-yl | 2 | H | H | $CH_3$ | |
| 5.18 | 2-Cl-pyrid-5-yl | 2 | H | H | $C_2H_5$ | |
| 5.19 | 2-Cl-pyrid-5-yl | 2 | H | H | $C_3H_7$-n | |
| 5.20 | 2-Cl-pyrid-5-yl | 2 | H | H | $CH_2CH=CH_2$ | |
| 5.21 | 2-Cl-pyrid-5-yl | 2 | H | H | $CH_2C\equiv CH$ | |
| 5.22 | 2-Cl-pyrid-5-yl | 2 | H | H | $C_4H_9$-n | |
| 5.23 | 2-Cl-thiazol-5-yl | 2 | H | H | H | |
| 5.24 | 2-Cl-thiazol-5-yl | 2 | H | H | $CH_3$ | |
| 5.25 | 2-Cl-pyrid-5-yl | 2 | $CH_3$ | H | H | |
| 5.26 | 2-Cl-pyrid-5-yl | 2 | H | $CH_3$ | H | |
| 5.27 | 2-Cl-pyrid-5-yl | 1 | H | H | benzyl | resin |

Example P16

3-(2-Chloropyrid-5-yl-methyl)-2-cyanimino-pyrrolidine

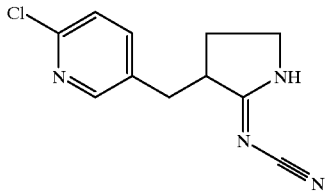

A mixture of 3.6 g of 3-(2-chloropyrid-5-yl-methyl)-pyrrolide-2-thione, 2.42 g of cyanamide and 30 ml of ethanol is boiled at reflux temperature for 90 minutes. The mixture is concentrated by evaporation in vacuo and the residue is chromatographed on silica gel using ethyl acetate/methanol (9:1) as eluant The title compound having a melting point of 137–140° C. (compound 6.3) is obtained.

Example P17

3-(2-Chloropyrid-5-yl-methyl)-1-methyl-2-cyanimino-pyrrolidine

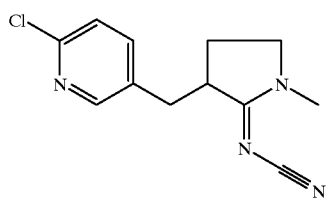

A mixture of 3.7 g of 3-(2-chloropyrid-5-yl-methyl)-1-methyl-2-methylthio-1-azacyclopent-1-enylium iodide and 2.5 g of cyanamide in 20 ml of ethanol is boiled at reflux for 6 hours. The mixture is concentrated by evaporation in vacuo and the residue is chromatographed on silica gel using dichloromethane/methanol (19:1) as eluant. The title compound having a melting point of 53–54° C. (compound 6.4) is obtained.

Example P18

The other compounds listed in Table 6 can be prepared in a manner analogous to that described in Examples P16 and P17.

TABLE 6

Compounds of the formula:

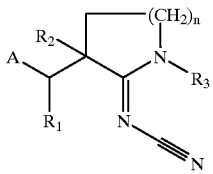

| Comp. No. | A | n | $R_1$ | $R_2$ | $R_3$ | Phys. data |
|---|---|---|---|---|---|---|
| 6.1 | pyrid-3-yl | 1 | H | H | H | |
| 6.2 | pyrid-3-yl | 1 | H | H | $CH_3$ | |
| 6.3 | 2-Cl-pyrid-5-yl | 1 | H | H | H | m.p. 137–140° C. |
| 6.4 | 2-Cl-pyrid-5-yl | 1 | H | H | $CH_3$ | m.p. 53–54° C. |
| 6.5 | 2-Cl-pyrid-5-yl | 1 | H | H | $C_2H_5$ | |
| 6.6 | 2-Cl-pyrid-5-yl | 1 | H | H | $C_3H_7$-n | |
| 6.7 | 2-Cl-pyrid-5-yl | 1 | H | H | $CH_2CH=CH_2$ | |
| 6.8 | 2-Cl-pyrid-5-yl | 1 | H | H | $CH_2C\equiv CH$ | |
| 6.9 | 2-Cl-pyrid-5-yl | 1 | H | H | $C_4H_9$-n | |
| 6.10 | 2-Cl-thiazol-5-yl | 1 | H | H | H | |
| 6.11 | 2-Cl-thiazol-5-yl | 1 | H | H | $CH_3$ | |
| 6.12 | 2-Cl-pyrid-5-yl | 1 | $CH_3$ | H | H | |
| 6.13 | 2-Cl-pyrid-5-yl | 1 | H | $CH_3$ | H | |
| 6.14 | pyrid-3-yl | 2 | H | H | H | |
| 6.15 | pyrid-3-yl | 2 | H | H | $CH_3$ | |
| 6.16 | 2-Cl-pyrid-5-yl | 2 | H | H | H | m.p. 169–171° C. |
| 6.17 | 2-Cl-pyrid-5-yl | 2 | H | H | $CH_3$ | |
| 6.18 | 2-Cl-pyrid-5-yl | 2 | H | H | $C_2H_5$ | |
| 6.19 | 2-Cl-pyrid-5-yl | 2 | H | H | $C_3H_7$-n | |
| 6.20 | 2-Cl-pyrid-5-yl | 2 | H | H | $CH_2CH=CH_2$ | |
| 6.21 | 2-Cl-pyrid-5-yl | 2 | H | H | $CH_2C\equiv CH$ | |
| 6.22 | 2-Cl-pyrid-5-yl | 2 | H | H | $C_4H_9$-n | |
| 6.23 | 2-Cl-thiazol-5-yl | 2 | H | H | H | |
| 6.24 | 2-Cl-thiazol-5-yl | 2 | H | H | $CH_3$ | |
| 6.25 | 2-Cl-pyrid-5-yl | 2 | $CH_3$ | H | H | |
| 6.26 | 2-Cl-pyrid-5-yl | 2 | H | $CH_3$ | H | |
| 6.27 | 2-Cl-pyrid-5-yl | 2 | H | $CH_3$ | benzyl | |

Example P19

The compounds listed in Table 7 can be prepared in a manner analogous to that described in Examples P1 to P18.

TABLE 7

Compounds of the formula:

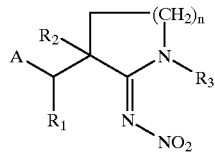

| Comp. No. | A | n | $R_1$ | $R_2$ | $R_3$ | Phys. data |
|---|---|---|---|---|---|---|
| 7.1 | pyrid-3-yl | 1 | H | H | H | |
| 7.2 | pyrid-3-yl | 1 | H | H | $CH_3$ | |
| 7.3 | 2-Cl-pyrid-5-yl | 1 | H | H | H | |
| 7.4 | 2-Cl-pyrid-5-yl | 1 | H | H | $CH_3$ | |
| 7.5 | 2-Cl-pyrid-5-yl | 1 | H | H | $C_2H_5$ | |
| 7.6 | 2-Cl-pyrid-5-yl | 1 | H | H | $C_3H_7$-n | |
| 7.7 | 2-Cl-pyrid-5-yl | 1 | H | H | $CH_2CH=CH_2$ | |
| 7.8 | 2-Cl-pyrid-5-yl | 1 | H | H | $CH_2C\equiv CH$ | |
| 7.9 | 2-Cl-pyrid-5-yl | 1 | H | H | $C_4H_9$-n | |
| 7.10 | 2-Cl-thiazol-5-yl | 1 | H | H | H | |
| 7.11 | 2-Cl-thiazol-5-yl | 1 | H | H | $CH_3$ | |

Formulation Examples (throughout, percentages are by weight)

| Example F1: Emulsifiable concentrates | a) | b) | c) |
|---|---|---|---|
| compound No. 1.2 | 25% | 40% | 50% |
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | 12% | — |
| cyclohexanone | — | 15% | 20% |
| xylene mixture | 65% | 25% | 20% |

Emulsions of any desired concentration can be prepared from such concentrates by dilution with water.

| Example F2: Solutions | a) | b) | c) | d) |
|---|---|---|---|---|
| compound No. 1.3 | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190° C.) | — | — | 94% | — |

These solutions are suitable for application in the form of microdrops.

| Example F3: Granules | a) | b) | c) | d) |
|---|---|---|---|---|
| compound No. 1.2 | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in dichloromethane, the solution is sprayed onto the carrier, and the solvent is subsequently evaporated off in vacuo.

| Example F4: Dusts | a) | b) |
|---|---|---|
| compound No. 1.2 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| Example F5: Wettable powders | a) | b) | c) |
|---|---|---|---|
| compound No. 1.2 | 25% | 50% | 75% |
| sodium lignosulfonate | 5% | 5% | — |
| sodium lauryl sulfate | 3% | — | 5% |
| sodium diisobutylnaphthalene-sulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is mixed with the adjuvants and the mixture is thoroughly ground in a suitable mill, affording wettable powders which can be diluted with water to give suspensions of any desired concentration.

| Example F6: Emulsifiable concentrate | |
|---|---|
| compound No. 1.3 | 10% |
| octylphenol polyethylene glycol ether (4-5 mol of ethylene oxide) | 3% |
| calcium dodecylbenzenesulfonate | 3% |
| castor oil polyglycol ether (36 mol of ethylene oxide) | 4% |

| Example F6: Emulsifiable concentrate | |
|---|---|
| cyclohexanone | 30% |
| xylene mixture | 50% |

Emulsions of any required concentration can be obtained from this concentrate by dilution with water.

| Example F7: Dusts | a) | b) |
|---|---|---|
| compound No. 1.2 | 5% | 8% |
| talcum | 95% | — |
| kaolin | — | 92% |

Ready-for-use dusts are obtained by mixing the active ingredient with the carrier and grinding the mixture in a suitable mill.

| Example F8: Extruder granules | |
|---|---|
| compound No. 1.3 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and granulated, and then dried in a stream of air.

| Example F9: Coated granules | |
|---|---|
| compound No. 1.2 | 3% |
| polyethylene glycol (mol. wt. 200) | 3% |
| kaolin | 94% |

The finely ground active ingredient is uniformly applied, in a mixer, to the kaolin moistened with polyethylene glycol Non-dusty coated granules are obtained in this manner.

| Example F10: Suspension concentrate | |
|---|---|
| compound No. 1.3 | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

Biological Examples (throughout, percentages are by weight, unless otherwise indicated)

Example B1

Action against *Anthonomus prandis*

Young cotton plants are sprayed with an aqueous emulsion comprising 400 ppm of test compound. After the spray coating has dried, the plants are populated with 10 *Anthonomus grandis* adults and placed in a plastics container. Evaluation is made 3 days later. The percentage reduction in the population and the percentage reduction in feeding damage (% activity) are determined by comparing the number of dead beetles and the feeding damage on the treated plants with that on untreated plants.

Compounds of Tables 5 to 7 exhibit good activity in this test. In particular, compounds 5.3, 5.4, 5.6 and 5.7 are more than 80% effective.

Example B2

Action against *Aphis craccivora*

Pea seedlings are infested with *Aphis craccivora*, then sprayed with a spray mixture comprising 400 ppm of test compound and then incubated at 20° C. Evaluation is made 3 to 7 days later. The percentage reduction in the population (% activity) is determined by comparing the number of dead Aphis craccivora individuals on the treated plants with that on untreated plants.

Compounds of Tables 5 to 7 exhibit good activity in this test. In particular, compound 5.3 is more than 80% effective.

Example B3

Action against *Bemisia tabaci*

Dwarf bean plants are placed in gauze cages and populated with adults of *Bemisia tabaci*. After oviposition, all the adults are removed. 10 days later the plants, with the Bemisia tabaci nymphs on them, are sprayed with an aqueous emulsion comprising 400 ppm of test compound. After a further 14 days, the percentage hatching rate of the eggs is evaluated in comparison with untreated control batches.

Compounds of Tables 5 to 7 exhibit good activity in this test. In particular, compounds 5.3, 5.4 and 5.6 are more than 80% effective.

Example B4

Systemic action against *Ctenocephalides felis* 20 adult fleas of the *Ctenocephalides felis* species are placed in a flat round cage closed on both sides with gauze. A vessel sealed on the underside with a parafilm membrane is placed on the cage. The vessel contains blood comprising 50 ppm of test compound and maintained at a constant 37°. The fleas ingest the blood through the membrane. Evaluation is made 24 and 48 hours after the start of the test. The percentage reduction in the population (% activity) is determined by comparing the number of dead Ctenocephalides felis fleas when treated blood is used with that when untreated blood is used. The blood is replaced by fresh treated blood 24 hours after treatment.

Compounds of Tables 5 to 7 exhibit good activity in this test. In particular, compound 5.3 is more than 80% effective.

Example B5

Action against *Diabrotica balteata*

Maize seedlings are sprayed with an aqueous emulsion comprising 400 ppm of test compound. After the spray coating has dried, the seedlings are populated with 10 *Diabrotica balteata* larvae in the second stage and placed in a plastics container. Evaluation is made 6 days later. The percentage reduction in the population (% activity) is determined by comparing the number of dead larvae on the treated plants with that on untreated plants.

Compounds of Tables 5 to 7 exhibit good activity in this test. In particular, compounds 5.3 to 5.7 and 5.16 are more than 80% effective.

Example B6

Action against *Heliothis virescens*

Young soybean plants are sprayed with an aqueous emulsion comprising 400 ppm of test compound. After the spray coating has dried, the plants are populated with 10 *Heliothis virescens* caterpillars in the first stage and placed in a plastics container. Evaluation is made 6 days later. The percentage reduction in the population and the percentage reduction in feeding damage (% activity) are determined by comparing the number of dead caterpillars and the feeding damage on the treated plants with that on untreated plants.

Compounds of Tables 5 to 7 exhibit good activity in this test. In particular, compound 5.3 is more than 80% effective.

Example B7

Ovo/larvicidal action against *Heliothis virescens*

Egg deposits of *Heliothis virescens* on cotton are sprayed with an aqueous emulsion comprising 400 ppm of test compound. 8 days later, the percentage of eggs which have hatched and the survival rate of the caterpillars are evaluated in comparison with untreated controls (% reduction in the population).

Compounds of Tables 5 to 7 exhibit good activity in this test

Example B8

Action against *Myzus persicae*

Pea seedlings are infested with *Myzus persicae*, then sprayed with a spray mixture comprising 400 ppm of test compound and then incubated at 20°. Evaluation is made 3 to 7 days later. The percentage reduction in the population (% activity) is determined by comparing the number of dead aphids on the treated plants with that on untreated plants.

Compounds of Tables 5 to 7 exhibit good activity in this test. In particular, compounds 5.3, 5.4, 5.6 and 5.16 are more than 80% effective.

Example B9

Systemic action against *Myzus persicae*

Pea seedlings are infested with *Myzus persicae*, then placed with their roots in a spray mixture comprising 400 ppm of test compound and then incubated at 20° C. Evaluation is made 3 to 7 days later. The percentage reduction in the population (% activity) is determined by comparing the number of dead aphids on the treated plants with that on untreated plants.

Compounds of Tables 5 to 7 exhibit good activity in this test. In particular, compounds 5.3, 5.4 and 5.6 are more than 80% effective.

Example B10

Action against *Nephotettix cincticeps*

Rice plants are sprayed with an aqueous emulsion comprising 400 ppm of test compound. After the spray coating has dried, the plants are populated with *Nephotettix cincti-* ceps larvae in the 2nd and 3rd stages. Evaluation is made 21 days later. The percentage reduction in the population (% activity) is determined by comparing the number of surviving leaf hoppers on the treated plants with that on untreated plants.

Compounds of Tables 5 to 7 exhibit good activity in this test. In particular, compounds 5.3, 5.4, 5.5 and 5.7 are more than 80% effective.

Example B11

Systemic action against *Nephotettix cincticeps*

Pots containing rice plants are placed in an aqueous emulsion solution comprising 400 ppm of test compound. The rice plants are then populated with *Nephotettix cincticeps* larvae in the 2nd and 3rd stages. Evaluation is made 6 days later. The percentage reduction in the population (% activity) is determined by comparing the number of leaf hoppers on the treated plants with that on untreated plants.

Compounds of Tables 5 to 7 exhibit good activity in this test. In particular, compounds 5.3, 5.4, 5.6, 5.7, 5.16 and 6.4 are more than 80% effective.

Example B12

Action against *Nilaparvata lugens*

Rice plants are sprayed with an aqueous emulsion comprising 400 ppm of test compound. After the spray coating has dried, the rice plants are populated with *Nilaparvata lugens* larvae in the 2nd and 3rd stages. Evaluation is made 21 days later. The percentage reduction in the population (% activity) is determined by comparing the number of surviving plant hoppers on the treated plants with that on untreated plants.

Compounds of Tables 5 to 7 exhibit good activity in this test. In particular, compounds 5.3, 5.4 and 5.7 are more than 80% effective.

Example B13

Systemic action against *Nilaparvata lugens*

Pots containing rice plants are placed in an aqueous emulsion solution comprising 10 ppm of test compound. The plants are then populated with *Nilaparvata lugens* larvae in the 2nd and 3rd stages. Evaluation is made 6 days later. The percentage reduction in the population (% activity) is determined by comparing the number of plant hoppers on the treated plants with that on untreated plants.

Compounds of Tables 5 to 7 exhibit good activity in this test. In particular, compounds 5.3, 5.4, 5.6, 5.7, 5.16 and 6.4 are more than 80% effective.

Example B14

Action against Spodoptera *littoralis caterpillars*

Young soybean plants are sprayed with an aqueous emulsion comprising 400 ppm of test compound. After the spray coating has dried, the soybean plants are populated with 10 Spodoptera *littoralis caterpillars* in the third stage and placed in a plastics container. Evaluation is made 3 days later. The percentage reduction in the population and the percentage reduction in feeding damage (% activity) are determined by comparing the number of dead caterpillars and the feeding damage on the treated plants with that on untreated plants.

Compounds of Tables 5 to 7 exhibit good activity against Spodoptera littoralis in this test. In particular, compounds 5.3 to 5.7 are more than 80% effective.

Example B15

Action against Plutella *xylostella caterpillars*

Young cabbage plants are sprayed with an aqueous emulsion comprising 400 ppm of test compound. After the spray coating has dried, the cabbage plants are populated with 10 Plutella *xylostella caterpillars* in the third stage and placed in a plastics container. Evaluation is made 3 days later. The percentage reduction in the population and the percentage reduction in feeding damage (% activity) are determined by comparing the number of dead caterpillars and the feeding damage on the treated plants with that on untreated plants.

Compounds of Tables S to 7 exhibit good activity against Plutella xylostella in this test In particular, compound 5.3 is more than 80% effective.

What is claimed is:

1. A compound of formula:

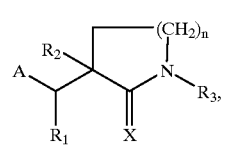

(I)

wherein

A is an unsubstituted or substituted aromatic or non-aromatic, monocyclic or bicyclic heterocyclic radical wherein the basic ring structure of A contains 1 hetero atom selected from nitrogen and consists of a ring having 6 ring members to which a further ring having 5 or 6 ring members may have been fused and wherein a ring nitrogen atom may have been replaced by a group

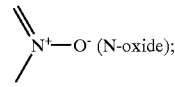

$R_1$ is hydrogen or $C_1$–$C_3$alkyl;
$R_2$ is hydrogen or $C_1$–$C_3$alkyl;
$R_3$ is hydrogen, an unsubstituted or substituted $C_1$–$C_6$alkyl, $C_3$–$C_6$cycloalkyl, $C_2$–$C_6$alkenyl or $C_2$–$C_6$alkynyl group, or C(=O)—$R_5$,
$R_5$ is $C_1$–$C_4$alkyl, $C_1$–$C_4$alkoxy, an unsubstituted or substituted phenyl, phenoxy or benzyloxy group, or N($R_6$)$_2$,
each $R_6$, independently of the other, is hydrogen, $C_1$–$C_4$alkyl or unsubstituted or substituted phenyl,
X is CH—NO$_2$, N—CN or N—NO$_2$ and
n is 2,
in free form or in salt form, or, where appropriate, a tautomer of such a compound or a salt thereof.

2. A compound according to claim 1 of formula I, wherein
A is an unsubstituted or mono- to tetra-substituted aromatic or non-aromatic, monocyclic or bicyclic heterocyclic radical wherein a ring nitrogen atom may have been replaced by a group

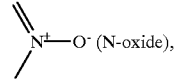

and wherein one or two of the substituents of A may be selected each independently of any other from the group consisting of $C_1$–$C_3$alkyl, halo-$C_1$–$C_3$alkyl, cyclopropyl, halocyclopropyl, $C_2$–$C_3$alkenyl, $C_2$–$C_3$alkynyl, halo-$C_2$–$C_3$alkenyl, halo-$C_2$–$C_3$alkynyl, hydroxy, mercapto, halo-$C_1$–$C_3$alkoxy, $C_1$–$C_3$alkylthio, halo-$C_1$–$C_3$alkylthio, allyloxy, propargyloxy, allylthio, propargylthio, haloallyloxy, haloallylthio, cyano and nitro, and from one to four of the substituents of A may be selected each independently of any other(s) from the group consisting of $C_1$–$C_3$alkyl, $C_1$–$C_3$alkoxy and halogen;

$R_1$ is hydrogen or $C_1$–$C_3$alkyl;

$R_2$ is hydrogen or $C_1$–$C_3$alkyl;

$R_3$ is hydrogen, $C_1$–$C_6$alkyl, halo-$C_1$–$C_6$alkyl, $C_1$–$C_6$alkoxy-$C_1$–$C_6$alkyl, $C_1$–$C_6$alkylthio-$C_1$–$C_6$alkyl, phenoxy-$C_1$–$C_6$alkyl, phenylthio-$C_1$–$C_6$alkyl, $C_3$–$C_6$cycloalkyl-$C_1$–$C_6$alkyl, benzyloxy-$C_1$–$C_6$alyl, di($C_1$–$C_4$alkyl)amino-$C_1$–$C_6$alkyl, cyano-$C_1$–$C_6$alkyl, $C_1$–$C_4$alkylcarbonyl-$C_1$–$C_6$alkyl, $C_1$–$C_4$alkoxycarbonyl-$C_1$–$C_6$alkyl, $C_3$–$C_6$cycloalkyl, halo-$C_3$–$C_6$cycloalkyl, $C_2$–$C_6$alkenyl, halo-$C_2$–$C_6$alkenyl, $C_2$–$C_6$alynyl, halo-$C_2$–$C_6$alkynyl or $C(=O)R_5$, $R_5$ is $C_1$–$C_4$alkyl, $C_1$–$C_4$alkoxy, phenyl, phenoxy or benzyloxy, or phenyl, phenoxy or benzyloxy substituted by from one to three substituents selected each independently of any other(s) from the group consisting of halogen, $C_1$–$C_4$alkyl, halo-$C_1$–$C_4$alkyl, $C_1$–$C_4$alkoxy, nitro and cyano, or is $N(R_6)_2$, each $R_6$, independently of the other, is hydrogen, $C_1$–$C_4$alkyl or phenyl, or phenyl substituted by from one to three substituents selected each independently of any other(s) from the group consisting of halogen, $C_1$–$C_4$alkyl, halo-$C_1$–$C_4$alkyl, $C_1$–$C_4$alkoxy, nitro and cyano, and X is CH—$NO_2$, N—CN or N—$NO_2$.

3. A compound according to claim 1 of formula I in free form.

4. A compound according to claim 1 of formula I wherein the basic ring structure of A is unsaturated.

5. A compound according to claim 1 of formula I wherein A is bonded via a carbon atom of its basic ring structure to the remainder of the compound of formula I.

6. A compound according to claim 1 of formula I wherein A is unsubstituted or mono- or di-substituted by substituents selected from the group consisting of halogen, —OH, —SH, $C_1$–$C_3$alkyl, halo-$C_1$–$C_3$alkyl, $C_1$–$C_3$alkoxy and halo-$C_1$–$C_3$alkoxy, and a ring nitrogen atom of A may have been replaced by

7. A compound according to claim 1 of formula I wherein A is pyridyl or 1-oxidopyridinio, each of which may be unsubstituted or substituted.

8. A compound according to claim 1 of formula I wherein $R_1$ is hydrogen or methyl.

9. A compound according to claim 1 of formula I wherein $R_2$ is hydrogen or methyl.

10. A compound according to claim 1 of formula I wherein $R_3$ is hydrogen, $C_1$–$C_6$alkyl, $C_3$–$C_6$cycloalkyl, $C_3$–$C_4$alkenyl or $C_3$–$C_4$alkynyl.

11. A compound according to claim 1 of formula I wherein X is CH—$NO_2$.

12. A compound according to claim 1 of formula I wherein X is N—CN.

13. A compound according to claim 1 of formula I wherein

A is a pyridyl or 1-oxidopyridinio bonded via a carbon atom of its basic ring structure to the remainder of the compound of formula I and unsubstituted or mono- or di-substituted by substituents selected from the group consisting of halogen and $C_1$–$C_3$alkyl, $R_1$ and $R_2$ are each independently of the other hydrogen or methyl, $R_3$ is hydrogen, $C_1$–$C_6$alkyl, $C_3$–$C_6$cycloalkyl, $C_3$–$C_4$alkenyl or $C_3$–$C_4$alkynyl, X is CH—$NO_2$ or N—CN.

14. A compound according to claim 13 of formula I wherein

A is pyrid-3-yl, 2-chloropyrid-5-yl, 1-oxido-3-pyridinio, 2-chloro-1-oxido-5-pyridinio or 2,3-dichloro-1-oxido-5-pyridinio and $R_3$ is hydrogen or $C_1$–$C_4$alkyl.

15. A compound according to claim 13 of formula I wherein

A is 2-chloropyrid-5-yl, $R_3$ is hydrogen or $C_1$–$C_4$alkyl and

X is CH—$NO_2$.

16. A compound according to claim 1 of formula I selected from the group consisting of the following compounds:

3-(2-chloropyrid-5-yl-methyl)-1-methyl-2-nitromethylidene-piperidine, 3-(2-chloropyrid-5-yl-methyl)-2-nitromethylidene-piperidine, 3-(2-chloropyrid-5-yl-methyl)-1-methyl-2-cyanimino-piperidine, 3-(2-chloropyrid-5-yl-methly)-2-cyanimino-piperidine.

17. A compound of formula:

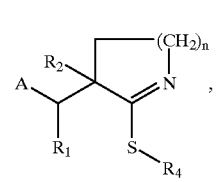

(IIa)

wherein A, $R_1$, $R_2$ and n are as defined in claim 1, formula I, and $R_4$ is $C_1$–$C_6$alkyl, or, where appropriate, a tautomer thereof, in each case in free form or in salt form.

18. A salt of formula:

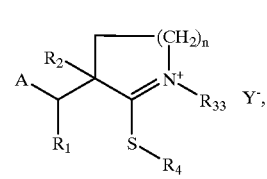

(IIb)

wherein A, $R_1$, $R_2$ and n are as defined in claim 1, formula I, $R_{33}$ has the definitions given for $R_3$ in formula I, claim 1, with the exception of hydrogen, and $Y^-$ is a counter ion, or a tautomer thereof.

19. A compound of formula:

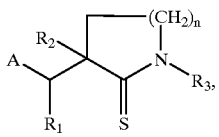

(III)

wherein A, $R_1$, $R_2$, $R_3$ and n are as defined in claim 1, formula I, and, where appropriate, the tautomer thereof, in each case in free form or in salt form.

20. A compound of formula:

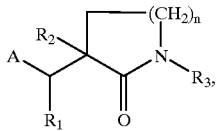

(VI)

wherein A, $R_1$, $R_2$, $R_3$ and n are as defined in claim 1, formula I, or, where appropriate, a tautomer thereof, in each case in free form or in salt form.

21. A pesticidal composition which comprises as active ingredient at least one compound as described in claim 1, formula I, or, where appropriate, a tautomer thereof, in each case in free form or in agrochemically acceptable salt form, and at least one adjuvant.

22. A composition according to claim 21 for controlling insects.

23. A process for the preparation of a composition as described in claim 21, which comprises intimately mixing and/or grinding the active ingredient with the adjuvant(s).

24. A method of controlling pests, which comprises applying to the pests, or to the locus thereof, a compound as described in claim 1, formula I, or a composition as described in claim 21.

25. A method according to claim 24 of controlling insects.

26. A method according to claim 24 of protecting plant propagation material against pests, which comprises treating the propagation material or the planting site thereof.

27. Plant propagation material treated in accordance with the method described in claim 26.

28. A process for the preparation of a compound of formula I of claim 1, which comprises either reacting a) a compound of formula:

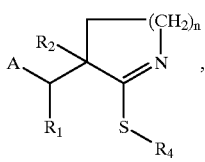

(IIa)

wherein A, $R_1$, $R_2$ and n are as defined above for formula I and $R_4$ is $C_1$–$C_6$alkyl, or a tautomer and/or a salt thereof, or b) for the preparation of a compound of formula I wherein $R_3$ is other than hydrogen, a salt of formula:

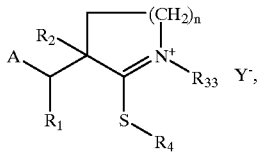

(IIb)

wherein A, $R_1$, $R_2$ and n are as defined in claim 1, formula I, $R_{33}$ has the definitions given for $R_3$ in claim 1, formula I, with the exception of hydrogen, $R_4$ is $C_1$–$C_6$alkyl and $Y^-$ is a counter ion, or, where appropriate, a tautomer thereof, or c) a compound of formula:

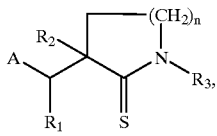

(III)

wherein A, $R_1$, $R_2$, $R_3$ and n are as defined in claim 1, formula I, or a tautomer and/or a salt thereof,
with nitromethane, cyanamide, a salt of nitromethane or of cyanamide or with ammonia and a nitration reagent, or d) for the preparation of a compound of formula I wherein $R_3$ is other than hydrogen, reacting a compound of formula:

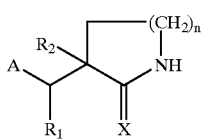

(Ia)

(obtainable, for example, in accordance with process a) or c)), wherein A, $R_1$, $R_2$, X and n are as defined in claim 1, formula I, or a salt thereof, with a compound of formula:

$Y-R_{33}$  (IV), wherein $R_{33}$ has the definitions given for $R_3$ in claim 1, formula I, with the exception of hydrogen, and Y is a leaving group.

29. The use of a compound as described in claim 1, formula I, or of a composition as described in claim 21, in a method as described in claim 24.

30. The use according to claim 29 for controlling insects.

* * * * *